US011312902B2

(12) United States Patent
Ishikawa et al.

(10) Patent No.: US 11,312,902 B2
(45) Date of Patent: Apr. 26, 2022

(54) ZINC OXIDE PHOSPHOR AND METHOD FOR PRODUCING SAME

(71) Applicant: Sakai Chemical Industry Co., Ltd., Sakai (JP)

(72) Inventors: Momoko Ishikawa, Osaka (JP); Keita Kobayashi, Osaka (JP); Nanae Ogata, Osaka (JP); Kenji Mori, Osaka (JP); Tomonori Tojo, Osaka (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 551 days.

(21) Appl. No.: 16/302,009

(22) PCT Filed: Jun. 30, 2017

(86) PCT No.: PCT/JP2017/024272
§ 371 (c)(1),
(2) Date: Nov. 15, 2018

(87) PCT Pub. No.: WO2018/004006
PCT Pub. Date: Jan. 4, 2018

(65) Prior Publication Data
US 2020/0308482 A1 Oct. 1, 2020

(30) Foreign Application Priority Data

Jun. 30, 2016 (JP) .................. 2016-130850
Oct. 17, 2016 (JP) .................. 2016-203888

(51) Int. Cl.
*C09K 11/54* (2006.01)
*A61K 8/27* (2006.01)

(52) U.S. Cl.
CPC ............... *C09K 11/54* (2013.01); *A61K 8/27* (2013.01); *A61K 2800/434* (2013.01)

(58) Field of Classification Search
CPC ....... C09K 11/54; C09K 11/883; C09K 11/70; C09K 11/56; C09K 11/06; C09K 11/584;
(Continued)

(56) References Cited

U.S. PATENT DOCUMENTS 2,529,711 A * 11/1950 Smith ............... C09K 11/54
 252/301.6 R
2,628,201 A * 2/1953 Smith ............... C09K 11/55
 252/301.6 R
(Continued)

FOREIGN PATENT DOCUMENTS

CN 1371339 9/2002
CN 1698170 11/2005
(Continued)

OTHER PUBLICATIONS

Zinc Products—Product details, "Aen Seihin Ichiran;" Sakai Chemical Industry Co., Ltd.; Mar. 2009, available at http://www.sakai-chem.co.jp/en/products/product_03_01.html, 10 pages. Attached English translation is not a direct translation, but it corresponds to the original reference.
(Continued)

*Primary Examiner* — Eisa B Elhilo
(74) *Attorney, Agent, or Firm* — Hamre, Schumann, Mueller & Larson, P.C.

(57) ABSTRACT

The present invention provides a method for easily and simply producing a zinc oxide phosphor that has a high level of safety and a high emission intensity and is useful for, for example, cosmetic applications. The present invention also provides a zinc oxide phosphor having such excellent physical properties and a cosmetic product containing the same. Provided is a method for producing a zinc oxide phosphor, including: a raw material mixing step of mixing an oxygen-containing zinc compound and a sulfur-containing compound; and a firing step of firing the raw material mixture (Continued)

Example 1    Example 2

Example 3    Example 4

Comparative Example 1    Comparative Example 2 obtained in the raw material mixing step, the firing step including firing in a reducing atmosphere followed by firing in an oxygen-containing atmosphere.

8 Claims, 9 Drawing Sheets

(58) Field of Classification Search
CPC . C09K 11/0811; C09K 11/623; C09K 11/595; C09K 11/7777; A61K 8/27; A61K 2800/434
USPC .................................................. 252/301.6 R
See application file for complete search history.

(56) References Cited

U.S. PATENT DOCUMENTS

| | | | | |
|---|---|---|---|---|
| 6,322,725 | B1* | 11/2001 | Yu | C09K 11/7414 252/301.6 R |
| 6,416,862 | B1 | 7/2002 | Kogoi et al. | |
| 6,699,371 | B2* | 3/2004 | Choi | C09K 11/54 204/192.15 |
| 8,384,284 | B2* | 2/2013 | Toda | C09K 11/7734 313/503 |
| 2005/0225520 | A1 | 10/2005 | Sugimoto et al. | |
| 2008/0258110 | A1* | 10/2008 | Oshio | C04B 35/584 252/301.6 R |

FOREIGN PATENT DOCUMENTS

| | | |
|---|---|---|
| CN | 1805902 | 7/2006 |
| JP | S63147823 | 6/1988 |
| JP | H02228389 | 9/1990 |
| JP | 03284613 A * | 12/1991 |
| JP | 05-117127 | 5/1993 |
| JP | 06-093259 | 4/1994 |
| JP | 10-087434 | 4/1998 |
| JP | 2000-247637 | 9/2000 |
| JP | 2004-269867 | 9/2004 |
| JP | 2010-037328 | 2/2010 |
| JP | 2013001578 | 1/2013 |
| JP | 2018-065780 | 4/2018 |
| WO | 2004108599 | 12/2004 |

OTHER PUBLICATIONS

Pharmacopoeia of People's Republic of China, 2010 Edition, Part 2, National Commission of Chinese Pharmacopoeia, First edition, published by China Medical Science and Technology Press, p. 820, publication date Jan. 31, 2010 with a partial translation.

Notification of partial revision to types of pigments, standards, and test methods for cosmetics (draft) Jun. 1, 2016 (487 pages), and concise explanation in English.

"Ruihetang Zinc Oxide Ointment," URL: https://detail.tmall.com/item.htm?spm=a230r.1.14.1.5e2e1d0cyajgaZ&id=619764439888&ns=1&abbucket=13, Retrieved from the Internet on Feb. 15, 2022 (10 pages including concise English explanation).

"Pharmacopoeia of the People's Republic of China, 2015 Edition, Part 2," the National Pharmacopoeia Committee, First Edition, China Medical Science and Technology Press, p. 1130 (6 pages including concise English explanation).

"Production and application of colored metal fine chemical products," SHU Wan-yin, Central South University of Technology Press, First Edition, pp. 119-124, published on Dec. 31, 1995 (11 pages including concise English explanation).

* cited by examiner

FIG.1
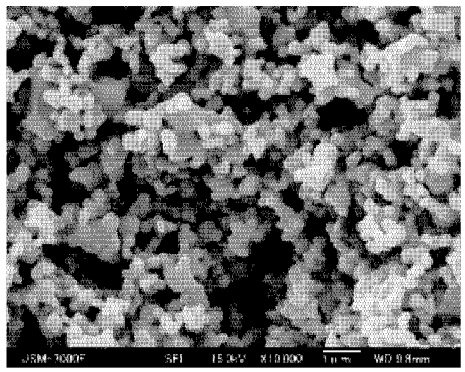
Example 1
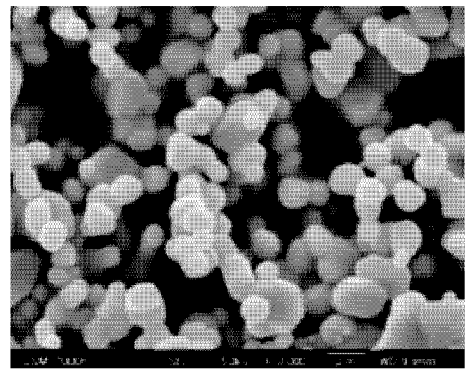
Example 2
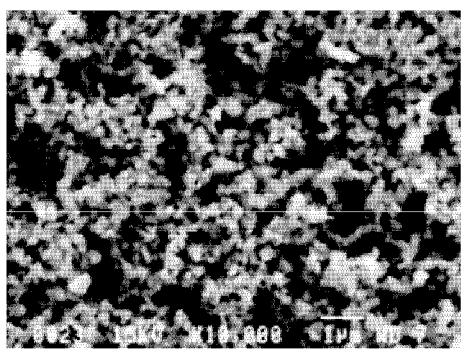
Example 3
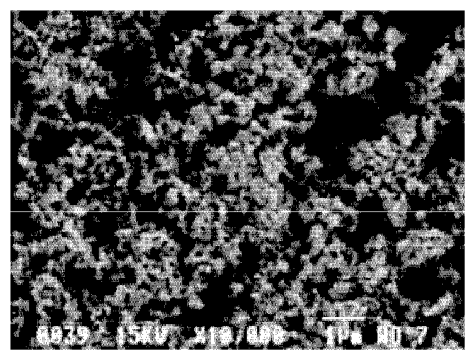
Example 4
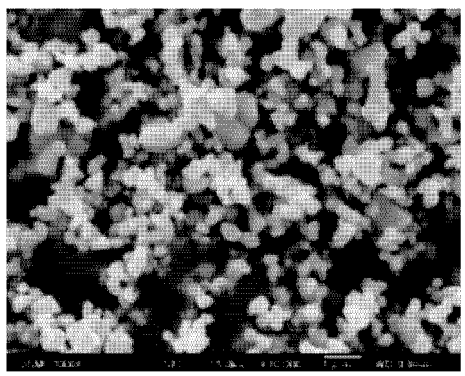
Comparative Example 1
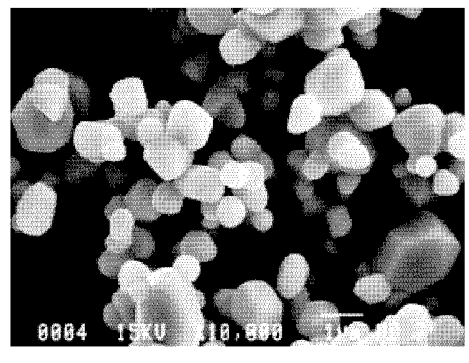
Comparative Example 2

FIG.8
(a)
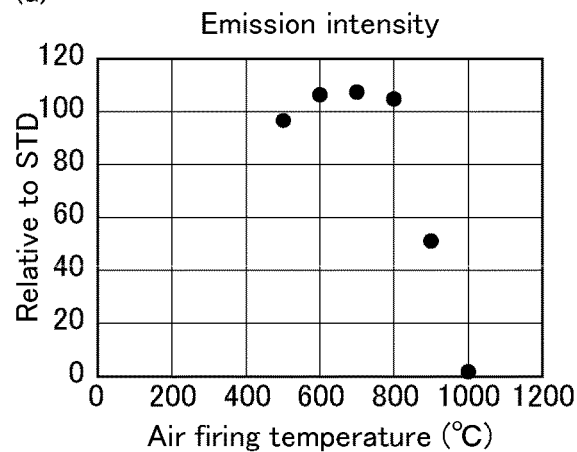
Emission intensity of STD: 100
(b)
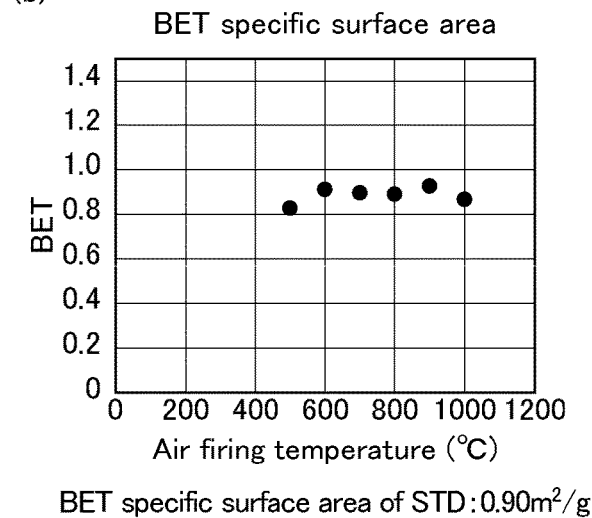
BET specific surface area of STD: 0.90 m²/g
(c)
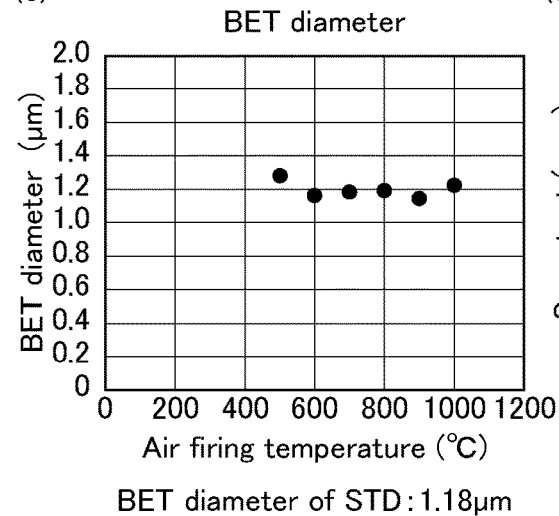
BET diameter of STD: 1.18 μm
(d)
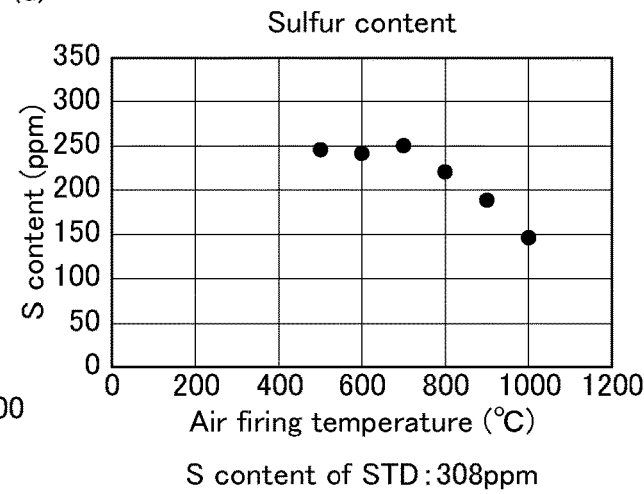
S content of STD: 308 ppm FIG.9
(a)
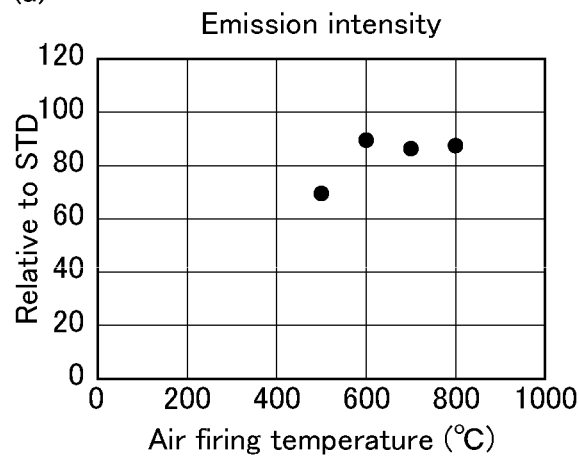
Emission intensity of STD:100
(b)
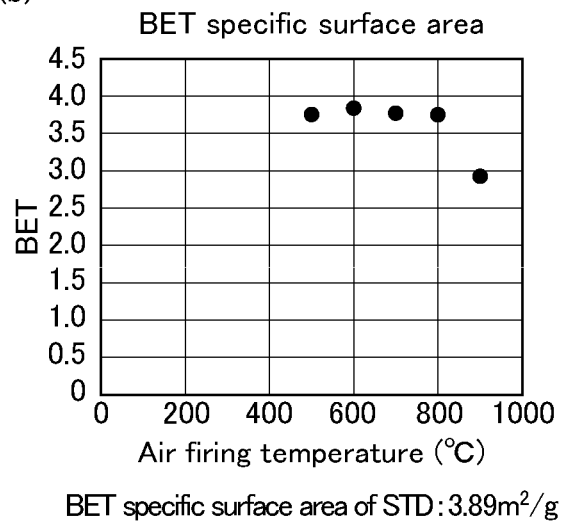
BET specific surface area of STD:3.89m²/g
(c)
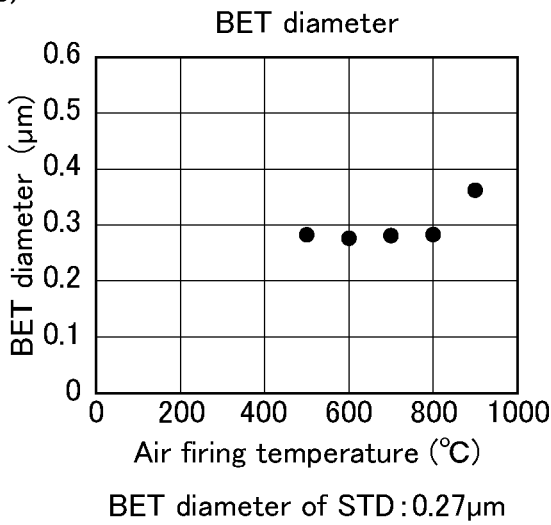
BET diameter of STD:0.27μm
(d)
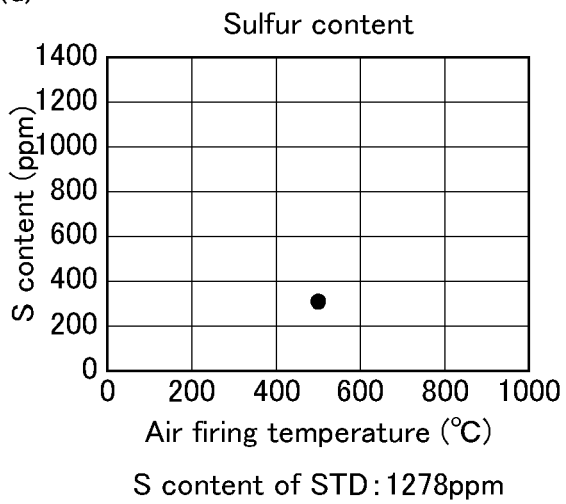
S content of STD:1278ppm FIG.11
(a)
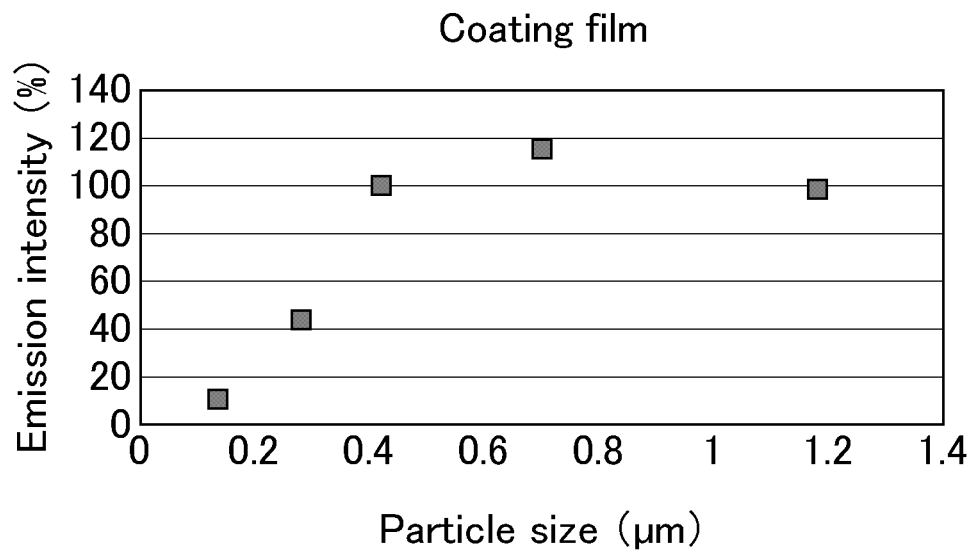
(b)
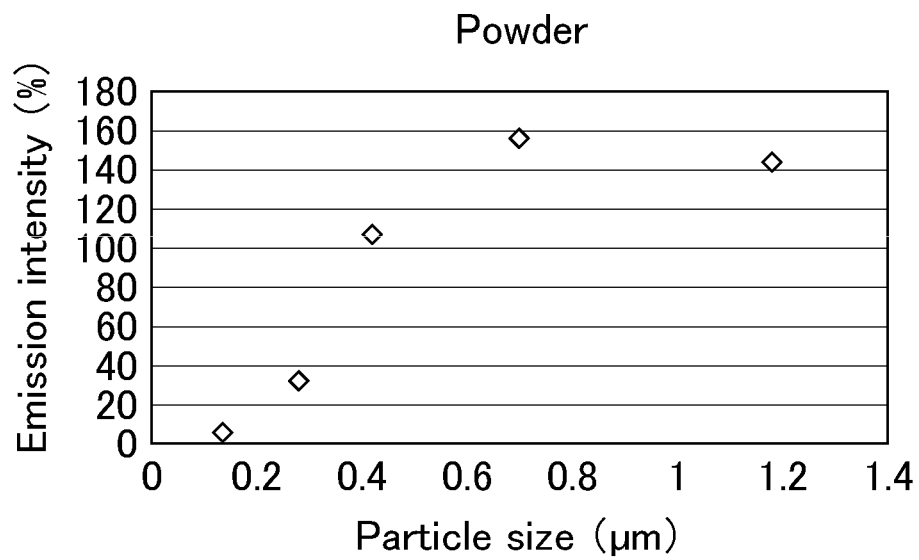

ZINC OXIDE PHOSPHOR AND METHOD FOR PRODUCING SAME

TECHNICAL FIELD

The present invention relates to zinc oxide phosphors and methods for producing the same.

BACKGROUND ART

Zinc oxide is a relatively inexpensive and stably supplied resource. Zinc oxide is used in various applications, including white pigment, transparent electrodes, and phosphors. In phosphor applications, oxygen-deficient zinc oxide phosphors obtained by reducing zinc oxide (ZnO) are usually used. They are considered to be represented by the average compositional formula $Zn_{1+z}O$ or $ZnO_{1-x}$. Patent Literature 1 discloses a method for producing such a zinc oxide phosphor. Patent Literature 2, for example, discloses use of a zinc oxide phosphor in cosmetic products.

CITATION LIST

Patent Literature

Patent Literature 1: JP H06-93259 A
Patent Literature 2: JP H05-117127 A

SUMMARY OF INVENTION

Technical Problem

As mentioned above, Patent Literature 2 discloses use of a zinc oxide phosphor in cosmetic products. However, conventional zinc oxide phosphors typified by those of Patent Literatures 1 and 2 can contain large amounts of impurities harmful to the human body, such as sulfide, thus raising safety concerns. There is room for improvement to achieve a zinc oxide phosphor suitable for cosmetic applications or other applications that require a high level of safety.

The present invention was made in view of the situation in the art. The present invention aims to provide a method for easily and simply producing a zinc oxide phosphor that has a high level of safety and a high emission intensity and is useful for, for example, cosmetic applications. The present invention also aims to provide a zinc oxide phosphor having such excellent physical properties and a cosmetic product including the zinc oxide phosphor.

Solution to Problem

The present inventors made studies on the method for producing a zinc oxide phosphor and focused on the fact that a zinc oxide phosphor is produced by adding a sulfur-containing compound to an oxygen-containing zinc compound (e.g., zinc oxide, zinc carbonate) and firing the mixture in a reducing atmosphere. The inventors found out that while the use of a sulfur-containing compound is necessary for sufficient emission intensity, use of a large amount of sulfur-containing compound results in a large sulfur content of the obtained zinc oxide phosphor and thus raises safety concerns. Further studies showed that when firing in an oxygen-containing atmosphere is performed after firing in a reducing atmosphere, it is possible to easily and simply produce a zinc oxide phosphor having a sufficiently high emission intensity and a sufficiently reduced sulfur content. The zinc oxide phosphor produced in this manner has a high enough level of safety to comply with specific requirements of Japanese Standards of Quasi-drug Ingredients (2006), and also has a small particle size to exhibit excellent dispersibility and UV blocking properties required in cosmetic applications, for example. The zinc oxide phosphor is thus particularly useful as a cosmetic raw material. The present inventors also found out that the production method can be effectively used not only for producing a zinc oxide phosphor that has a small particle size, but also for producing a zinc oxide phosphor that has a moderate particle size but is uniform in particle size and excellent in safety and emission intensity. The inventor thus arrived at a solution of the above issue, completing the present invention.

The present invention includes a method for producing a zinc oxide phosphor, including: a raw material mixing step of mixing an oxygen-containing zinc compound and a sulfur-containing compound; and a firing step of firing the raw material mixture obtained in the raw material mixing step, the firing step including firing in a reducing atmosphere followed by firing in an oxygen-containing atmosphere.

The firing in an oxygen-containing atmosphere is preferably performed at a firing temperature of 500° C. or higher and lower than 1000° C. At such a firing temperature, the resulting zinc oxide phosphor can have a higher level of safety and a higher emission intensity and also has a smaller particle diameter.

The zinc oxide phosphor is preferably a cosmetic raw material.

The present invention also includes a method for producing a solid cosmetic product, including the step of mixing raw materials including a zinc oxide phosphor obtained by the production method, talc, sericite, and an oil component and compression-molding the raw material mixture.

The present invention also includes a zinc oxide phosphor which complies with the purity requirements of "Carbonate, and clarity and color of solution" and "Lead" specified in "Zinc Oxide" in Japanese Standards of Quasi-drug Ingredients (2006).

That is, the present invention includes a zinc oxide phosphor which satisfies the following: when 2.0 g of the zinc oxide phosphor is shaken with 10 mL of pure water, followed by addition of 30 mL of 10% sulfuric acid and heating on a water bath with stirring, no effervescence occurs or the solution is clear and colorless; and when 20 mL of pure water is added to 2.0 g of the zinc oxide phosphor, followed by addition, with stirring, of 5 mL of glacial acetic acid and heating on a water bath to effect dissolution, addition of five drops of a potassium chromate reagent to the solution after cooling produces no turbidity or cloudiness.

The zinc oxide phosphor preferably has a BET diameter of 1.2 μm or smaller. A zinc oxide phosphor with such a BET diameter has excellent dispersibility and UV blocking properties.

The present invention also includes a solid cosmetic product containing the zinc oxide phosphor.

Advantageous Effects of Invention

With the above structure, the method for producing a zinc oxide phosphor of the present invention can easily and simply produce a zinc oxide having a high level of safety and a high emission intensity. This zinc oxide phosphor is particularly useful as a cosmetic raw material. A zinc oxide phosphor having a small particle size produced by the method is particularly excellent in dispersibility and UV blocking properties and thus very useful as a cosmetic raw material.

BRIEF DESCRIPTION OF DRAWINGS

FIG. 1 shows SEM photographs of phosphors (powders) obtained in Examples 1 to 4 and Comparative Examples 1 and 2.

FIG. 8 shows graphs of the relation between the air firing temperature and phosphor physical properties in Example 2 (Example 7).

FIG. 9 shows graphs of the relation between the air firing temperature and phosphor physical properties in Example 3 (Example 8).

FIG. 11 shows graphs for investigation of the relation between the BET diameter of a phosphor and the emission intensity of the phosphor or a coating film produced therefrom. The graphs are based on the results shown in Table 2.

DESCRIPTION OF EMBODIMENTS

Figure 2:
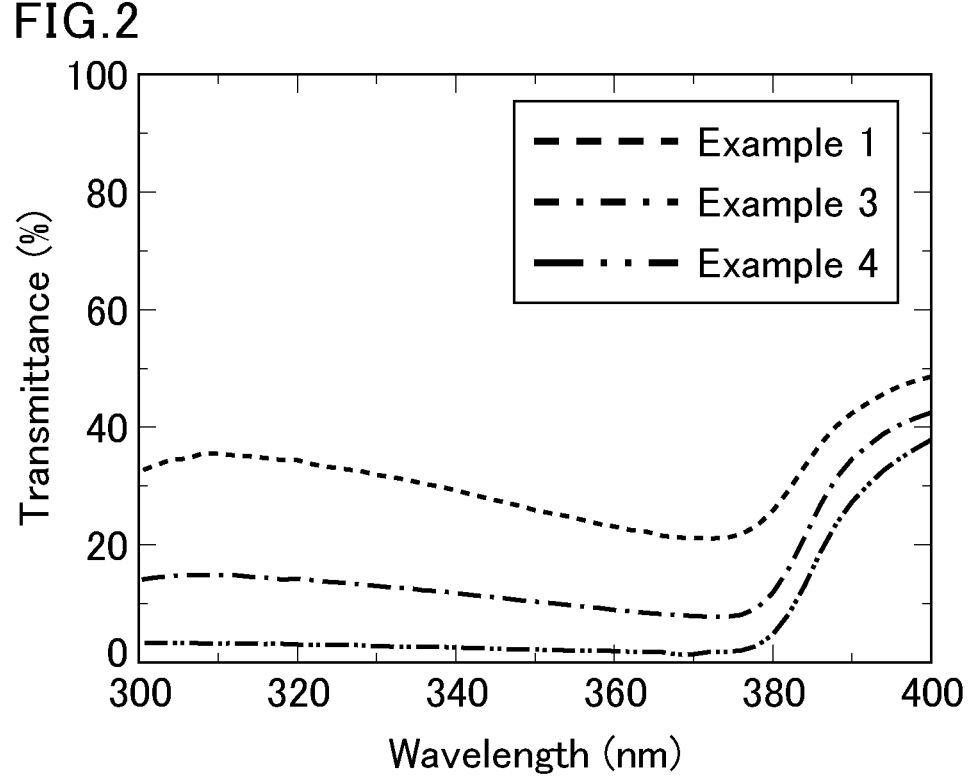
FIG. 2 shows transmittance spectra of the phosphors obtained in Examples 1, 3 and 4 in evaluation of UV blocking performance.

Preferred embodiments of the present invention will be described in detail below. The present invention should not be limited to the description below, and appropriate modifications can be made without changing the gist of the present invention.
1. Method for Producing Zinc Oxide Phosphor First, the method for producing a zinc oxide phosphor, which is a first aspect of the present invention, will be described.

The method for producing a zinc oxide phosphor of the present invention includes: a raw material mixing step of mixing an oxygen-containing zinc compound and a sulfur-containing compound; and a firing step of firing the raw material mixture obtained in the raw material mixing step. The method may further include any one or two or more steps performed in usual phosphor production other than the above steps. The steps will be further described below.
—Raw Material Mixing Step—

In the raw material mixing step, an oxygen-containing zinc compound and a sulfur-containing compound are mixed. If necessary, a raw material other than the oxygen-containing zinc compound and sulfur-containing compound may be further added. Each raw material may be used singly, or two or more kinds may be used. The raw materials will be first described.

The oxygen-containing zinc compound may be any compound containing an oxygen atom and a zinc atom. Preferred examples of the oxygen-containing zinc compound include zinc oxide, zinc carbonate, and zinc hydroxide. More preferred among them are zinc oxide and zinc carbonate from the viewpoint of reactivity.

The sulfur-containing compound may be any compound containing a sulfur atom. Preferred examples of the sulfur-containing compound include sulfide salts and sulfuric acid salts. Preferred examples of the salts include metal salts, ammonium salts, and organic amine salts. Specifically, examples of the metal atoms constituting the metal salts include: monovalent metals such as sodium, lithium, potassium, rubidium, and cesium; divalent metals such as zinc, magnesium, calcium, strontium, and barium; trivalent metals such as aluminum; and other metals such as iron and titanium. Examples of the organic amine groups constituting the organic amine salts include alkanolamine groups such as a monoethanolamine group, a diethanolamine group, and a triethanolamine group; alkylamine groups such as a monoethylamine group, a diethylamine group, and a triethylamine group; and polyamine groups such as an ethylenediamine group and a triethylenediamine group. Preferred salts include metal salts, with zinc salts being more preferred. That is, particularly preferred sulfur-containing compounds are zinc sulfide and zinc sulfate.

The mixing ratio of the oxygen-containing zinc compound and the sulfur-containing compound is not limited. For example, the amount of sulfur atoms relative to 100 mol % of the oxygen-containing zinc compound is preferably 0.01 to 10 mol %. When the amount of sulfur atoms is within this range, the resulting zinc oxide phosphor can have a sufficient emission intensity while achieving both a small particle size (or uniform particle size) and safety in a more balanced manner. The amount of sulfur atoms is more preferably 0.05 to 3 mol %, still more preferably 0.07 to 1 mol %.

In the raw material mixing step, the raw materials may be mixed by any method. The raw materials may be mixed by wet mixing or dry mixing, but are preferably mixed by dry mixing from the viewpoint of simplifying the firing step. The dry mixing may be performed with a ball mill, a blender, or the like.

In the raw material mixing step, a flux may further be added, if necessary. In such a case, the zinc oxide phosphor obtained through the firing step (described later) can have a moderate particle size (e.g., a BET diameter of greater than 1.2 μm) while having a uniform particle size, and can also have excellent safety and emission intensity. A preferred embodiment of the present invention is a method for producing a zinc oxide phosphor, including a raw material mixing step of mixing an oxygen-containing zinc compound, a sulfur-containing compound, and a flux and a firing step of firing the raw material mixture obtained in the raw material mixing step, the firing step including firing in a reducing atmosphere followed by firing in an oxygen-containing atmosphere.

Any flux may be used. Examples thereof include potassium carbonate, sodium carbonate, sodium hydrogen carbonate, potassium chloride, sodium chloride, magnesium chloride, calcium chloride, ammonium chloride, potassium fluoride, sodium fluoride, calcium fluoride, magnesium fluoride, aluminum fluoride, ammonium fluoride, magnesium bromide, calcium bromide, ammonium bromide, magnesium iodide, calcium iodide, ammonium iodide, sodium hydroxide, potassium hydroxide, boric acid, and sodium borate. These may be used alone or in combination of two or more thereof.

If the flux is used, the amount of the flux is not limited, and may be appropriately determined according to the desired particle size. For example, the amount of the flux is preferably 0.01 to 20 mol %, more preferably 0.02 to 10 mol % relative to 100 mol % of the oxygen-containing zinc compound.

—Firing Step—

In the firing step, the mixture obtained in the mixing step is fired. The firing step includes firing in a reducing atmosphere followed by firing in an oxygen-containing atmosphere. The firing in a reducing atmosphere is hereinafter also referred to as "reduction firing". The firing in an oxygen-containing atmosphere is hereinafter also referred to as "oxygen firing". Each firing may be performed by any method, and may be performed by a fluidized-bed firing method or a fixed bed firing method.

In the reduction firing, the reducing atmosphere is not limited. Examples thereof include a mixed gas atmosphere of hydrogen and nitrogen and a mixed gas atmosphere of carbon monoxide and nitrogen. From the viewpoint of safety and cost, a mixed gas atmosphere of hydrogen and nitrogen is preferred. In this case, the hydrogen content in the mixed gas is preferably 0.1 to 20% by volume, more preferably 0.5 to 10% by volume.

In the reduction firing, the firing temperature is preferably 500° C. or higher and lower than 1000° C. At such a firing temperature, it is easy to produce a zinc oxide phosphor that is improved in crystallinity to the extent that it can achieve a sufficient emission intensity, smaller in particle size, dense and high in emission intensity. The firing temperature is more preferably 600° C. to 950° C., still more preferably 700° C. to 900° C.

To reduce uneven firing, firing is preferably performed such that the temperature distribution is uniform.

In the reduction firing, the firing time is preferably 0.5 to 12 hours. With such a firing time, it is easy to produce a zinc oxide phosphor that is improved in crystallinity to the extent that it can achieve a sufficient emission intensity, smaller in particle size, dense and high in emission intensity. Firing for longer than 12 hours does not have a proportional effect and may not increase the productivity. The firing time is preferably 12 hours or shorter, more preferably 0.5 to 5 hours.

When the reduction firing is repeated multiple times, the total firing time of the repeated firing is preferably within the above preferable firing time range.

The "firing temperature" herein means a maximum achieved temperature in firing. The "firing time" herein means the time during which the maximum achieved temperature is held, and does not include the heat-up time before the maximum temperature is reached.

In the present invention, the reduction firing and the oxygen firing each may be repeated two or more times, or the reduction firing may be performed after the oxygen firing, and then the oxygen firing may be performed again. In either case, for improved physical properties of the zinc oxide phosphor, the last firing in the firing step is preferably the oxygen firing. After the reduction firing or before or after the oxygen firing, treatment such as repulping (e.g., slurrying the fired product followed by stirring), filtration, washing with water, grinding, or drying may be performed, if necessary.

The oxygen-containing atmosphere in the oxygen firing may be any atmosphere that contains oxygen. The oxygen-containing atmosphere is preferably an atmosphere containing 1% by volume or more oxygen, more preferably an atmosphere containing 10% by volume or more oxygen, still more preferably an air atmosphere.

The oxygen firing is preferably performed at a firing temperature of 500° C. or higher and lower than 1000° C. At such a firing temperature, the zinc oxide phosphor can achieve a higher level of safety and a more sufficient emission intensity. The upper limit of the firing temperature is more preferably 950° C. or lower, still more preferably 900° C. or lower, particularly preferably 850° C. or lower, most preferably 800° C. or lower from the viewpoint of further improving the emission intensity of the zinc oxide phosphor and achieving a smaller particle size or a more uniform particle size. The lower limit of the firing temperature is more preferably 550° C. or higher, still more preferably 600° C. or higher from the viewpoint of even further improving the safety and the emission intensity. In the present invention, the firing temperature in the oxygen firing is particularly preferably 600° C. or higher and 800° C. or lower.

To reduce uneven firing, firing is preferably performed such that the temperature distribution is uniform.

In the oxygen firing, the firing time is preferably 0.5 to 12 hours. With such a firing time, the resulting zinc oxide phosphor can have higher whiteness and a higher level of safety. Firing for longer than 12 hours does not have a proportional effect and may not increase the productivity. The firing time is preferably 12 hours or shorter, more preferably 0.5 to 5 hours.

When the oxygen firing is repeated multiple times after the reduction firing, the total firing time of the repeated firing is preferably within the above preferable firing time range.

—Grinding Step—

In the present invention, if necessary, grinding or classification may be performed before or after the reduction firing or the oxygen firing. In particular, grinding is preferably performed after the reduction firing but before the oxygen firing. The grinding may be either wet grinding or dry grinding, but preferably is dry grinding. The dry grinding may be performed with a dry grinding machine such as a roll mill, a hammer mill, a fluid energy mill, or a muller mixer, if necessary.

—Post-Treatment Step—

In the present invention, if necessary, the fired product obtained in the firing step may be subjected to a post-treatment such as repulping (e.g., slurrying the fired product followed by stirring), filtration, washing with water, grinding, or drying. If necessary, classification may be performed with a sieve. The sieve classification may be wet or dry classification, for example.

—Different Element Adding Step—

In the present invention, a step of adding a different element may be further performed, if necessary. Addition of a different element gives other characteristics derived from the element to the zinc oxide phosphor, making the phosphor useful for various applications. The different element adding step may be performed at any stage of the production method of the present invention. Specifically, the step may be performed before the firing step, during the firing step (e.g., between the reduction firing and the oxygen firing, or at the same time with these firings), after the firing step, or before or after the post-treatment step. The different element adding step is preferably performed before the firing step. In cases where a flux is used in the mixing step as described above, the mixing step may correspond to the "different element adding step".

The different element means an element other than zinc. Examples thereof include alkali metals such as Li, Na, and K; alkaline earth metals such as Be, Ca, Sr, Ba, and Ra; and other metals and nonmetals such as Y, Zr, V, Nb, Cr, Mo, W, Fe, Co, Ni, Pd, Pt, Cu, Ag, Zn, B, Al, Ga, Si, Ge, Sn, Pb, P, and Gd. These may be added within the range that does not affect safety to the human body or the performance. Two or more elements may be added.

For example, addition of Ca (calcium) tends to cause particles to grow in a pillar shape, so that the zinc oxide phosphor can exhibit properties (e.g., smoothness) derived from the shape. Addition of K (potassium) tends to promote the particle growth, so that the zinc oxide phosphor can exhibit properties derived from the size (e.g., infrared blocking performance). The final zinc oxide phosphor may contain the different element or may not contain it because of, for example, a water washing step.

The different element may be added by any method. For example, an aqueous solution of a water-soluble salt of the different element to be added may be prepared. The aqueous solution is wet-mixed with the target to which the different element is to be added (for example, a raw material used in the firing step, a fired product, or a precursor, though depending on the stage at which the different element adding step is performed) and the mixture is dried by evaporation. Alternatively, a solid oxide or hydroxide of the different element may dry-mixed with the target. Further, these mixtures may be fired so that the different element enters the zinc oxide phosphor crystal to form a solid solution. In the present invention, the different element is particularly preferably added by mixing the flux describe above. An embodiment of the production method in which a flux is further added in the mixing step (i.e., a method for producing a zinc oxide phosphor, including a raw material mixing step of mixing an oxygen-containing zinc compound, a sulfur-containing compound, and a flux and a firing step of firing the raw material mixture obtained in the raw material mixing step, the firing step including firing in a reducing atmosphere followed by firing in an oxygen-containing atmosphere) is also particularly preferred.

The amount of the different element to be added is not limited. The different element is usually preferably added in such an amount that the emission properties of the zinc oxide phosphor are not affected and the different element can exhibit its effects. Though depending on the type of the different element and the intended purpose, for example, the amount of the different element to be added is preferably adjusted such that the amount of the different element is 0.01 to 20 mol % relative to 100 mol % of the oxygen-containing zinc compound as a raw material, or in cases where the different element adding step is performed after firing, relative to 100 mol % of the fired product before the addition of the different product.

—Surface Treatment Step—

In the present invention, the zinc oxide phosphor may be surface-treated, if necessary. That is, the production method of the present invention may further include a surface treatment step. The surface treatment step is preferably performed after the firing step (if steps such as the post-treatment step are performed after the firing step, after these steps).

The method for the surface treatment is not limited, and various conventionally known surface treatments may be performed. For example, a coating can be formed on the surface treatment target (e.g., the firing product obtained in the firing step, or if a post-treatment step is performed, the resulting treated product) by adding a surface treatment agent to an aqueous dispersion of the target and then optionally adjusting the pH. If a water-insoluble organic compound is used, the organic compound may be added by a dry method and subjected to grinding and mixing and, if necessary, heating.

The surface treatment agent is not limited. The surface can be treated with any substance. For example, a substance that can be used in cosmetic products may be used when the resulting zinc oxide phosphor is to be used in cosmetic applications. Examples of the surface treatment agent include inorganic compounds and organic compounds. One of them may be used alone, or two or more of them may be combined and formed into layers or mixed. Although a coating layer of an organic compound may be formed after a treatment with an inorganic compound, it is important that the inherent emission of the zinc oxide phosphor is not impaired.

Specific examples of the surface treatment agent include inorganic compounds such as oxides, hydroxides, carbonates, and phosphates of silicon, zinc, titanium, aluminum, zirconium, and tin. With these surface treatment agents, a zinc oxide phosphor having a coating layer thereof can be obtained. Examples of surface treatment agents for giving water repellency include dimethylpolysiloxane, methylhydrogenpolysiloxane, methylphenylpolysiloxane, methylmethoxypolysiloxane, dimethylpolysiloxane dihydrogen, and copolymers thereof, stearic acid, lauric acid, oleic acid, and metal salts thereof (e.g., aluminum salt, zinc salt, magnesium salt, and calcium salt), polyvinyl alcohol, ethylene glycol, propylene glycol, monoethanolamine, aminomethylpropanol, diethanolamine, triethanolamine, monopropanolamine, dipropanolamine, tripropanolamine, paraffin wax, polyethylene wax, aminosilane, epoxysilane, methacrylsilane, vinylsilane, mercaptosilane, chloroalkylsilane, alkylsilane, fluoroalkylsilane, hexamethylsilazane, hexamethylcyclotrisilazane, trimethylolpropane, trimethylolethane, and pentaerythritol.

The amount of the surface treatment agent to be used is not limited. For example, the amount is preferably adjusted such that the amount of the coating of the surface treatment agent is within the range of 0.1 to 30% by mass relative to 100% by mass of the final zinc oxide phosphor. When the amount of the coating is 0.1% by mass or more, the surface treatment can exhibit the performance improving effect. When the amount of the coating is 30% by mass or less, the treatment does not impair the inherent emission characteristics and also has an economic advantage. The amount of the coating is more preferably within the range of 0.1 to 20% by mass.

2. Zinc Oxide Phosphor

Next, the zinc oxide phosphor, which is a second aspect of the present invention, will be described.

The zinc oxide phosphor of the present invention complies with the purity requirements of "Carbonate, and clarity and color of solution" and "Lead" specified in "Zinc Oxide" in Japanese Standards of Quasi-drug Ingredients (2006). The zinc oxide phosphor can be easily and simply produced by the production method of the present invention.

The zinc oxide phosphor preferably has a BET diameter of 1.2 µm or smaller. A zinc oxide phosphor having such a BET diameter can exhibit dispersibility and UV blocking properties and thus can be useful as a cosmetic raw material, for example. The BET diameter is more preferably 1.15 µm or smaller, still more preferably 1.1 µm or smaller. The lower limit thereof is not limited, but is preferably 0.1 µm or greater, more preferably 0.2 μm or greater, still more preferably 0.4 μm or greater from the viewpoint of the handleability.

In the present invention, it is also preferred that the zinc oxide phosphor has a BET diameter of greater than 1.2 μm. A zinc oxide phosphor having such a BET diameter can exhibit infrared blocking properties and thus is suitable as an optical material and the like as well as a cosmetic raw material. From the viewpoint of the infrared blocking properties, the BET diameter is more preferably 2.0 μm or greater. From the viewpoint of better texture (e.g., less rough feel upon application to the skin in a cosmetic use), the BET diameter is preferably 20 μm or smaller, more preferably 10 μm or smaller.

The zinc oxide phosphor having a BET diameter of greater than 1.2 μm more preferably has a highly uniform particle size.

The BET diameter herein is an average primary particle size (equivalent diameter) calculated from a BET specific surface area value assuming that the particles are spherical. Specifically, the BET diameter can be determined by the method described in Examples below.

The particle size of the zinc oxide phosphor is preferably set in view of the balance between the particle size and the number of particles per unit area in the respective usage forms of the zinc oxide phosphor. Such setting allows the zinc oxide phosphor to exhibit a particularly high emission intensity in the respective usage forms. For example, when the zinc oxide phosphor of the present invention is used in cosmetic applications (e.g., cream or emulsion), particularly, the BET diameter of the zinc oxide phosphor is preferably 1.2 μm or smaller, more preferably 1.15 μm or smaller, still more preferably 1.1 μm or smaller. The lower limit is preferably 0.1 μm or greater, more preferably 0.2 μm or greater, still more preferably 0.4 μm or greater.

The zinc oxide phosphor preferably has a $D_{50}$ of 3 μm or smaller. A zinc oxide having such a $D_{50}$ can exhibit higher dispersibility and UV blocking properties and thus is more useful as a cosmetic raw material and the like. The $D_{50}$ is more preferably smaller than 3 μm. The lower limit thereof is not limited, but is preferably 0.3 μm or greater, more preferably 1 μm or greater from the viewpoint of the handleability.

The $D_{50}$ herein is a particle size value at which the integral value is 50% on a particle number-based particle size distribution curve determined with Microtrac (laser diffraction/scattering method). Specifically, the $D_{50}$ can be determined by the method described in Examples described below.

The $D_{50}$ determined by this method represents the primary particle size or the secondary particle size, but it is difficult to determine which of them the $D_{50}$ represents only by the numerical value. The results of microscopic observation (see, for example, FIG. 1), however, indicate that the $D_{50}$ obtained for the zinc oxide phosphor of the present invention is the $D_{50}$ of the secondary particle size.

The zinc oxide phosphor complies with the purity requirements of "Carbonate, and clarity and color of solution" and "Lead" specified in "Zinc Oxide" in Japanese Standards of Quasi-drug Ingredients (2006). That is, the zinc oxide phosphor satisfies the following: when 2.0 g of the zinc oxide phosphor is shaken with 10 mL of pure water, followed by addition of 30 mL of 10% sulfuric acid and heating on a water bath with stirring, no effervescence occurs or the solution is clear and colorless; and when 20 mL of pure water is added to 2.0 g of the zinc oxide phosphor, followed by addition, with stirring, of 5 mL of glacial acetic acid and heating on a water bath to effect dissolution, addition of five drops of a potassium chromate reagent to the solution after cooling produces no turbidity or cloudiness.

The zinc oxide phosphor also complies with the purity requirement of "Carbonates and substances insoluble in acids" specified in "Zinc Oxide" in European Pharmacopeia, which will be described in Examples below.

The zinc oxide phosphor has excellent safety and thus can be suitably used in applications where strict safety standards must be met, such as cosmetic products, medicines, and quasi-drugs. The zinc oxide phosphor particularly preferably complies with all the requirements specified in "Zinc Oxide" in this standard.

The zinc oxide phosphor may have any shape. Examples of the shape include a spherical shape (including a substantially spherical shape), a rod shape, a needle shape, a spindle shape, a flake shape, a hexagonal flake shape, a hexagonal pillar shape, a needle-shaped aggregate, an integrated flake type, and an irregular shape. The shape can be observed with a scanning electron microscope, for example.

The zinc oxide phosphor may contain a different element. In such a case, the zinc oxide phosphor can exhibit other characteristics derived from the different element and thus is useful for wider applications. The different element is as described above.

The zinc oxide phosphor may be used in various applications (e.g., cosmetic products) without any treatment, but may be surface-treated. The surface treatment is as described above.

The zinc oxide phosphor preferably has a maximum emission wavelength (dominant wavelength) within the range of 480 to 540 nm when excited with light at a wavelength of 365 nm. A zinc oxide phosphor with a maximum emission wavelength within this wavelength range can emit green light. Green light has a high luminosity factor and thus is easy for the human eye to see. Such a zinc oxide phosphor is more useful as a phosphor. The dominant wavelength under these conditions is more preferably 500 to 520 nm.

The maximum emission wavelength (dominant wavelength) herein can be determined by the method described in Examples below.

The zinc oxide phosphor preferably has an internal quantum efficiency of 1% or higher. A zinc oxide phosphor having such an internal quantum efficiency is useful as a phosphor. The internal quantum efficiency is more preferably 5% or higher, still more preferably 10% or higher, particularly preferably 15% or higher, most preferably 20% or higher.

The internal quantum efficiency can be determined by the method described in Examples below.

The zinc oxide phosphor preferably has a BET specific surface area of 0.1 to 20 $m^2/g$. For example, a zinc oxide phosphor having such a specific surface area and a small particle size (e.g., a BET diameter of 1.2 μm or smaller) is less likely to precipitate when dispersed in a dispersion solvent, thus providing a dispersion having excellent long-term stability. A zinc oxide phosphor having such a specific surface area and a great particle size (e.g., a BET diameter of greater than 1.2 μm) has better infrared blocking properties and texture, and also can have less effect on the human body. The specific surface area is more preferably 0.8 to 10 $m^2/g$.

The BET specific surface area herein can be determined by the method described in Examples below.

The zinc oxide phosphor is white. The zinc oxide phosphor preferably has a whiteness in the W value of 85 or higher. A zinc oxide phosphor having such a W value is less likely to absorb generated fluorescence and thus can achieve good phosphor performance. The W value is more preferably 95 or higher. In the production method of the present invention, since reduction firing is followed by oxygen firing, the W value can be increased by 0.5% or more as compared with a zinc oxide phosphor obtained by reduction firing alone. The W value is preferably increased by 1% or more.

The W value is calculated by Formula (1) below from the hunter color values L (lightness), a (chroma), and b (hue).

$$W=100-\{(100-L)^2+(a^2+b^2)\}^{1/2} \quad (1)$$

The zinc oxide phosphor preferably has a S content of 300 ppm or less, more preferably 280 ppm or less, still more preferably 260 ppm or less. Herein, S analysis can be performed by the method described in Examples below.

The zinc oxide phosphor obtained by the first aspect (production method) of the present invention and the zinc oxide phosphor of the second aspect both have a high level of safety. Especially with a small particle size, the zinc oxide phosphors also have excellent dispersibility and UV blocking properties. The zinc oxide phosphors are thus preferably incorporated in cosmetic products, medicines, quasi-drugs, radiation shielding materials, coating materials, resin materials, catalysts, toners for printing, lubricants, and other products. The zinc oxide phosphors are particularly preferably incorporated in cosmetic products. Accordingly, the zinc oxide phosphors are preferably cosmetic raw materials. A cosmetic product containing the above zinc oxide phosphor is one aspect of the present invention.

3. Cosmetic Product

Next, the cosmetic product, which is a third aspect of the present invention, will be described.

The cosmetic product of the present invention contains the zinc oxide phosphor of the present invention. The cosmetic product may be produced by any method, and may be produced by a usual method for producing a cosmetic product.

For production of a solid cosmetic product, raw materials including the zinc oxide phosphor of the present invention, talc, sericite, and squalane may be mixed and the raw material mixture may be compression-molded. The raw materials may be mixed by any method. They may be mixed with a grinding machine, a ball mill, a V blender, or a super mixer. The compression molding may be performed by any method, such as dry press molding.

The cosmetic product is not limited. Examples thereof include makeup products such as a foundation, a makeup base, an eye shadow, a blush, a mascara, and a lipstick, sunscreen agents, skincare products, haircare products, and UV protection products. In such cases, the cosmetic product is useful as a fluorescent cosmetic product. The cosmetic product of the present invention is particularly suitably used in makeup cosmetic products including a foundation, a makeup base, and an eye shadow and sunscreen agents. The cosmetic product of the present invention can be of any type. It may be an oil-based cosmetic, a water-based cosmetic, an O/W type cosmetic or a W/O type cosmetic. The cosmetic may be in any form. For example, it may be in a liquid form, an emulsion form, a cream form, a solid form, a paste form, a gel form, a multilayer form, a mousse form, or a spray form.

The cosmetic product preferably contains the zinc oxide phosphor in a proportion of 0.1 to 90% by mass relative to 100% by mass of the cosmetic product. If the amount is less than 0.1% by mass, the effects may not be sufficiently obtained. If the amount is more than 90% by mass, for example, the cosmetic product disadvantageously contains too much powder to contain sufficient liquid components. Such a cosmetic product is less flexible in formulation and hard to handle. The amount is more preferably 0.1 to 50% by mass, still more preferably 0.1 to 30% by mass.

The cosmetic product may contain one or two or more components other than the zinc oxide phosphor of the present invention, if necessary. Examples of other component include, but not limited to, organic solvents, dispersing agent, and any aqueous components and oil components usually used in the cosmetic field. Specific example thereof include oils; surfactants; moisturizers; higher alcohols; sequestrant; polymers (natural, semisynthetic, synthetic, or inorganic, water- or oil-soluble polymers); UV blocking agents; other drug components; various extracts; inorganic and organic pigments; inorganic and organic clay minerals and other various powders; inorganic and organic pigments treated with metallic soap or silicone; coloring materials such as organic dyes; preservatives; antioxidants; dyes; thickeners; pH adjusters; perfumes; cooling-sensation agents; astringents; disinfectants; and skin activators. The amounts of these components are not limited as long as they do not interfere with the effects of the present invention.

The oil is not particularly limited, and examples thereof include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerin, glycerin trioctanoate, glycerin triisopalmitate, cacao butter, coconut oil, horse fat, palm oil, beef tallow, mutton tallow, palm kernel oil, lard, beef bone fat, Japan wax kernel oil, hydrogenated beef tallow, hydrogenated oils such as hydrogenated coconut oil and hydrogenated castor oil, neatsfoot oil, Japan wax, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, microcrystalline wax, and squalane.

Examples of the surfactant include lipophilic nonionic surfactants, hydrophilic nonionic surfactants, and other surfactants. The lipophilic nonionic surfactant is not particularly limited, and examples thereof include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerin sorbitan penta-2-ethylhexylate, and diglycerin sorbitan tetra-2-ethylhexylate; glycerin polyglycerin fatty acids such as glycerin monocottonseed oil fatty acid, glycerin monoerucate, glycerin sesquioleate, glycerin monostearate, α,α'-glycerin oleate pyroglutamate, and glycerin monostearate malate; propylene glycol fatty acid esters such as propylene glycol monostearate; hydrogenated castor oil derivatives; and glycerin alkyl ethers.

The hydrophilic nonionic surfactant is not particularly limited, and examples thereof include POE sorbitan fatty acid esters such as POE sorbitan monooleate, POE sorbitan monostearate, and POE sorbitan tetraoleate; POE sorbitol fatty acid esters such as POE sorbitol monolaurate, POE sorbitol monooleate, POE sorbitol pentaoleate, and POE sorbitol monostearate; POE glycerin fatty acid esters such as POE glycerin monostearate, POE glycerin monoisostearate, and POE glycerin triisostearate; POE fatty acid esters such as POE monooleate, POE distearate, POE monodioleate, and ethylene glycol distearate; POE alkyl ethers such as POE lauryl ether, POE oleyl ether, POE stearyl ether, POE behenyl ether, POE 2-octyldodecyl ether, and POE cholestanol ether; POE alkyl phenyl ethers such as POE octyl phenyl ether, POE nonyl phenyl ether, and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin, and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives such as POE sorbitol beeswax; alkanolamides such as coconut oil fatty acid diethanolamide, lauric acid monoethanolamide, and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants.

The moisturizer is not particularly limited, and examples thereof include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerin (EO) PO adducts, *Rosa roxburghii* extract, yarrow extract, melilot extract, and 1,3-butylene glycol.

The higher alcohol is not particularly limited, and examples thereof include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers such as sodium alginate and propylene glycol alginate.

The synthetic water-soluble polymer is not particularly limited, and examples thereof include vinyl polymers such as polyvinyl alcohol, polyvinyl methyl ether, and polyvinyl pyrrolidone; polyoxyethylene polymers such as polyethylene glycol 20000, polyethylene glycol 40000, and polyethylene glycol 60000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof include bentonite, magnesium aluminum silicate (Veegum), laponite, hectorite, and silicic anhydride.

The UV blocking agent is not particularly limited, and examples thereof include benzoic acid-based UV blocking agents such as paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based UV blocking agents such as homomenthyl-N-acetyl anthranilate; salicylic acid-based UV blocking agents such as amyl salicylate, menthyl salicylate, homomenthyl salicylate, octyl salicylate, phenyl salicylate, benzyl salicylate, and p-isopropanol phenyl salicylate; cinnamic acid-based UV blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl-mono-2-ethylhexanoyl-diparamethoxy cinnamate; benzophenone-based UV blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotrialzole, 2-(2'-hydroxy-5'-t-octylphenyl)benzotriazole, 2-(2'-hydroxy-5'-methylphenyl) benzotriazole, dibenzalazine, dianisoylmethane, 4-methoxy-4'-t-butyldibenzoylmethane, and 5-(3,3-dimethyl-2-norbornylidene)-3-pentan-2-one.

Other components are not particularly limited, and examples thereof include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α- tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor; sulfur, lysozyme chloride, and pyridoxine chloride.

The extracts are not particularly limited, and examples thereof include *Houttuynia cordata* extract, *Phellodendron* bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of the powders include bright coloring pigments such as red oxide, yellow iron oxide, black iron oxide, mica titanium, iron oxide-coated mica titanium, and titanium oxide-coated glass flakes, inorganic powders such as those of mica, talc, kaolin, sericite, titanium dioxide, and silica, and organic powders such as polyethylene powder, nylon powder, crosslinked polystyrene, cellulose powder, and silicone powder. Preferably, part or all of the powder component is subjected to a known hydrophobization treatment with a substance such as a silicone, a fluorine compound, a metallic soap, an oily agent, or an acyl glutamic acid salt for improvement of sensory characteristics and improvement of makeup retainability.

EXAMPLES

Figure 3:
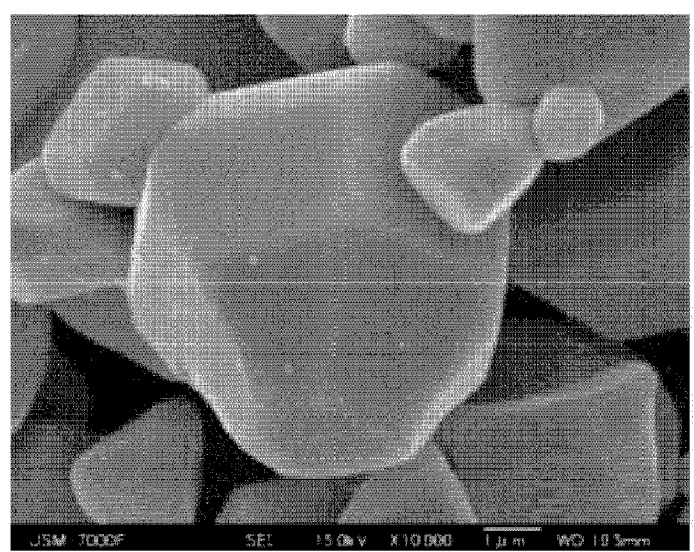
FIG. 3 shows a SEM photograph of Phosphor G obtained in Example 5.
Figure 6:
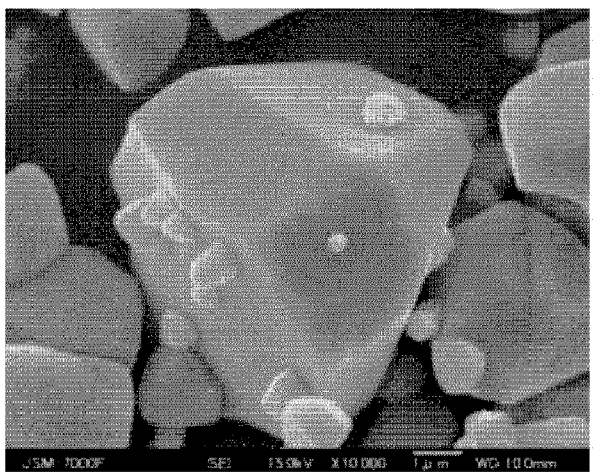
FIG. 6 shows a SEM photograph of Phosphor H obtained in Comparative Example 3.
Figure 7:
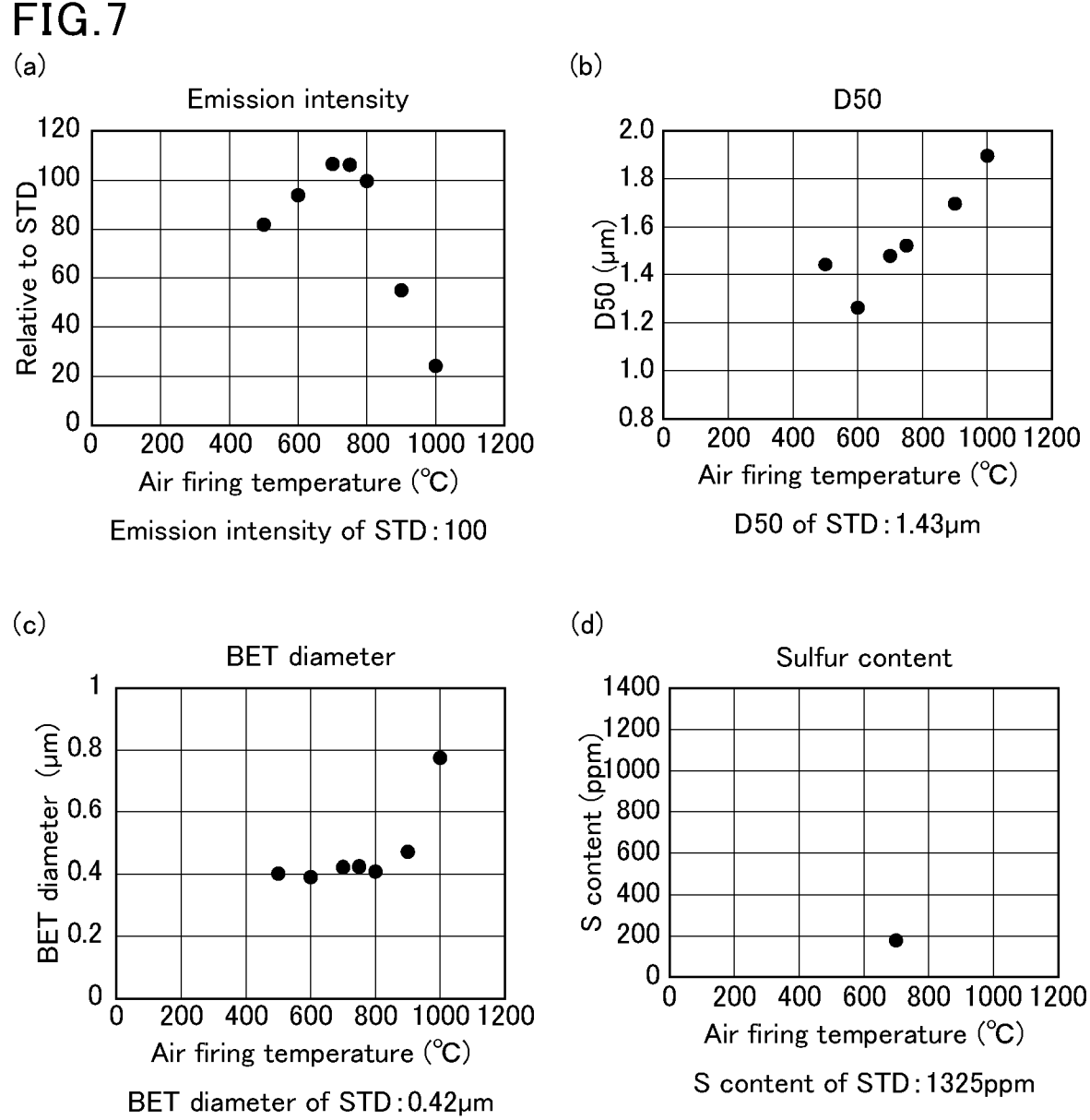
FIG. 7 shows graphs of the relation between the air firing temperature and phosphor physical properties in Example 1 (Example 6).

The present invention will be described in detail with reference to examples below. The present invention should not be limited to these examples. The physical properties were evaluated as follows.
1. Photoluminescence (PL) Evaluation Emission properties (emission intensity and dominant wavelength) of a sample (phosphor, cream, or coating film) as an evaluation target were determined with a fluorescence spectrophotometer (FP-6500, Jasco Corporation). Fluorescent integrating sphere model ISF-513 was used. The value of voltage of the photomultiplier tube (PMT) was set at 340. The maximum emission wavelength (dominant wavelength) and emission intensity when the sample was excited with light at wavelength of 365 nm were determined. Tables 1 and 2 and FIGS. 7 to 11 show the results.
2. Measurement of Internal Quantum Efficiency The internal quantum efficiency of each powder (phosphor) was measured with QE-2000 (Otsuka Electronics Co., Ltd). The measurement was performed in the wavelength range of 300 to 420 nm in 5-nm steps. Table 1 shows the results.
3. SEM Observation The surface of each powder were observed with a scanning electron microscope (JSM-840F and JSM-7000F, JEOL Ltd.). FIGS. 1, 3, and 6 show the obtained micrographs (SEM photographs).

4.1. Test in Accordance with Standards of Quasi-Drug Ingredients

Each powder was subjected to the tests described in the sections on purity requirements of "Carbonate, and clarity and color of solution" and "Lead" specified in "Zinc Oxide" in Japanese Standards of Quasi-drug Ingredients (2006). Specifically, the following tests were performed. Table 1 shows the results.
(1) Dilute Sulfuric Acid Dissolution Test An amount of 2.0 g of the powder is shaken with 10 mL of pure water, followed by addition of 30 mL of 10% sulfuric acid and heating on a water bath with stirring. When no effervescence occurs or the solution is clear and colorless (expressed as "Dissolved" in Table 1), the powder complies with the requirement.
(2) Acetic Acid Dissolution Test An amount of 20 mL of pure water was added to 2.0 g of the powder, followed by addition, with stirring, of 5 mL of glacial acetic acid and heating on a water bath to effect dissolution. When addition of five drops of a potassium chromate reagent to the solution after cooling produces no turbidity or cloudiness (expressed as "Dissolved" in Table 1), the powder complies with the requirement.

These tests correspond to the tests of the "Carbonate, and color and clarity of solution" and "Lead" sections among the purity tests specified in "Zinc Oxide" in Types, Standards, and Test Methods of Cosmetic Color Additives under the Korean Cosmetic Act. These tests also correspond to the test of the "LEAD" section and the test using "CARBONATE AND COLOR OF SOLUTION" in the "IRON AND OTHER HEAVY METALS" section among the purity tests specified in "Zinc Oxide" in United States Pharmacopeia.
4.2. European Pharmacopeia Each powder was subjected to the test of the "Carbonates and substances insoluble in acids" section specified in "ZINC OXIDE" in European Pharmacopeia. Specifically, the following test was performed.
(1) Dilute Hydrochloric Acid Dissolution Test An amount of 1 g the powder is dissolved in 15 mL of dilute hydrochloric acid. When it dissolves without effervescence and the solution is colorless, the powder complies with the requirement.
5. Average Particle Size $D_{50}$ The particle size distribution of each powder was determined with a laser diffraction particle size distribution measuring apparatus (Microtrac MT3000, Nikkiso Co., Ltd.) and a particle size distribution curve was obtained. Specifically, first, the target powder was put in the apparatus to achieve a transmittance of 0.7 to 0.99. Measurement was performed at a flow rate of 60% with ultrasonic dispersion and circulation. The circulating water in the apparatus during measurement was water. On the particle number-based particle size distribution curve, the particle size value at which the integrated value was 50% was taken as the average particle size $D_{50}$ (μm). Table 1 shows the results.
6. BET Specific Surface Area and BET Diameter (1) The BET specific surface area (SSA) was measured under the following conditions. Tables 1, 3, and 4 show the results.
—Measurement Conditions—
Device: Macsorb Model HM-1220, Mountech Co. Ltd.
Atmosphere: nitrogen ($N_2$) gas
Conditions for degassing with external degassing device: 105° C., 15 min
Conditions for degassing with the main specific surface area measuring device: 105° C., 5 min (2) The BET diameter was calculated from the obtained BET specific surface area using Formula (2) below, wherein the zinc oxide density is 5.67 g/cm$^3$.

BET diameter=2×3/(BET specific surface area×zinc oxide density)     (2)

7. Sulfur Content

The S analysis was performed by burning the sample in a combustion device and determining the S ion content by ion chromatography under the following conditions. Table 1 shows the results.
Automatic combustion device: NSX-2100 series Model AQF-2100H, Mitsubishi Chemical Analytech Co., Ltd.
Ion chromatograph: Nippon Dionex K.K.
Atmosphere: Ar 200 mL/min, O$_2$ 400 mL/min
Combustion temperature: 1100° C.
Concentration of samples for calibration curves: SO$_4^{2-}$ (ppm)=0.5, 1, 2, or 5

The samples for calibration curves were added such that the concentration of P as the internal standard was 1 ppm.

8. Crystallinity

The powder X-ray diffraction pattern (also referred to simply as an X-ray diffraction pattern) was determined and the full width at half maximum of the peak was calculated.
—Analysis Conditions—
Device: RINT-Ultima III, Rigaku Corp.
X-ray source: CuKα
Voltage: 50 kV
Current: 300 mA
Sample rotational speed: 60 rpm
Divergence slit: 1.00 mm
Divergence vertical slit: 10 mm
Scatter slit: open
Receiving slit: open
Scan mode: FT
Counting time: 1.0 sec
Step width: 0.0200°
Scan axis: 2θ/θ
Scan range: 10.0000 to 60.0000°

9. UV Blocking Performance

The UV blocking properties (UV blocking performance) were determined as follows.

An amount of 2.36 g of the powder, 5.5 g of alkyd resin varnish (BECKOSOL J-524, Dainippon Ink and Chemicals, Incorporated), 2.8 g of melamine resin vanish (SUPER BECKAMINE J-820, Dainippon Ink and Chemicals, Incorporated), and 5.7 g of xylene (JIS guaranteed reagent) were mixed. The powder was dispersed using a paint conditioner with 30 g of glass beads (1.5 mmφ) for 10 minutes, whereby a coating dispersion was prepared. Then, a small amount of the coating dispersion was sampled on a glass plate and formed into a film with a No. 12 bar coater. The film was baked at 130° C. for 30 minutes, whereby an evaluation film was obtained. The evaluation film was set in the measurement cell of a spectrophotometer (spectrophotometer model V-570 and integrating sphere model ILN-472, Jasco Corporation) and the transmittance of the film was measured with the spectrophotometer.

FIG. 2 shows the results (300 to 400 nm) of the phosphors obtained in Examples 1, 3, and 4.

10. Infrared Blocking Performance

The infrared blocking properties (infrared blocking performance) were determined as follows.

The powder was set in the measurement cell of a spectrophotometer (spectrophotometer model V-570 and integrating sphere model ILN-472, Jasco Corporation) and the reflectance of the powder was measured with the spectrophotometer.

Figure 5:
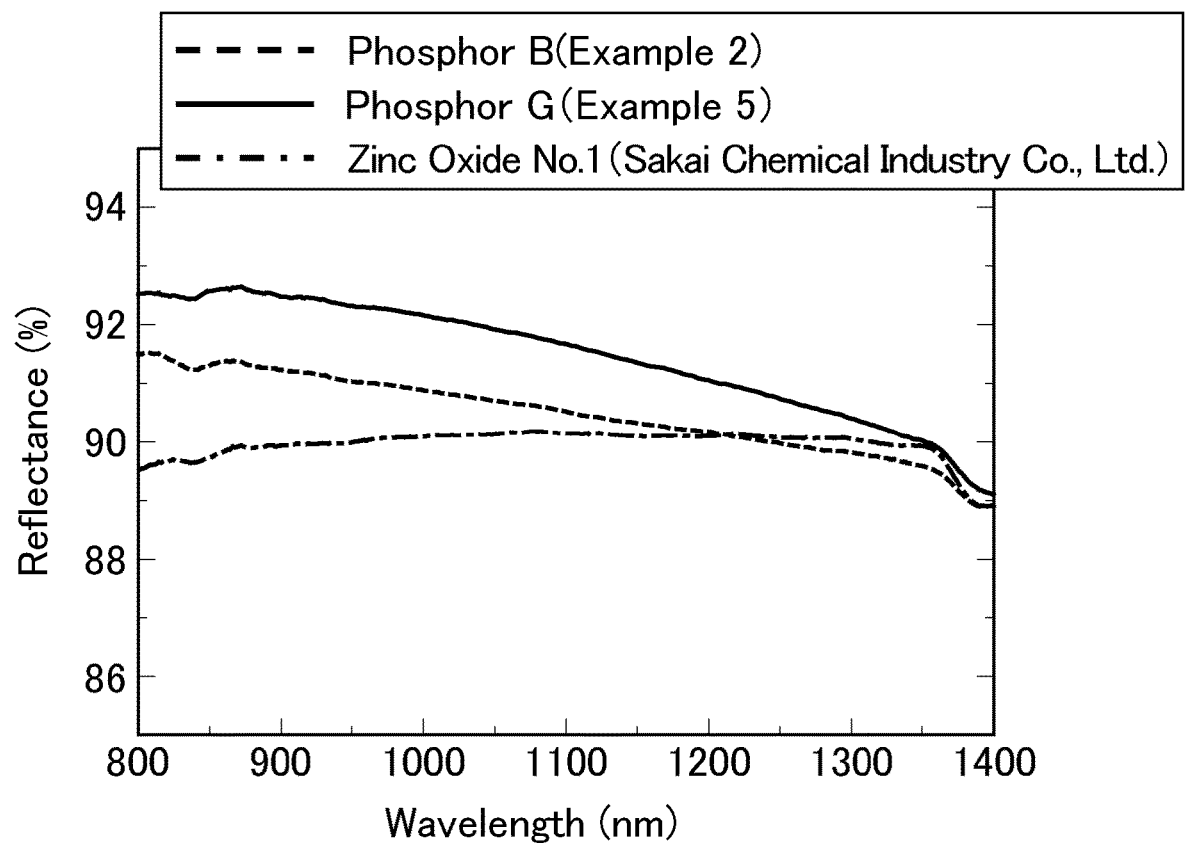
FIG. 5 shows reflectance spectra of the phosphors obtained in Examples 2 and 5 in evaluation of infrared blocking performance. For comparison, FIG. 5 also shows a reflectance spectrum of commercially available zinc oxide ("Zinc Oxide No. 1 (JIS)", Sakai Chemical Industry Co., Ltd.).

FIG. 5 shows the results (800 to 1400 nm) of the phosphors obtained in Examples 2 and 5. FIG. 5 also shows a reflectance spectrum of commercially available zinc oxide ("Zinc Oxide No. 1 (JIS)", Sakai Chemical Industry Co., Ltd.) for comparison.

11. Smoothness (MIU and MMD)

The smoothness of each sample was evaluated as follows.

Double-stick tape was attached to a slide. About half a spoonful of the powder (sample) was put on the adhesive surface and spread with a cosmetic sponge. A friction member was set on the sample. The slide was moved, and the average friction coefficient MIU and the fluctuation MMD of the average friction coefficient were measured from the load applied to the friction member. The measurement was performed with a friction tester (KES-SE, Kato Tech Co., Ltd.).

12. Dispersibility

An amount of 2.36 g of the powder, 5.5 g of alkyd resin varnish (BECKOSOL J-524, Dainippon Ink and Chemicals, Incorporated), 2.8 g of melamine resin varnish (SUPER BECKAMINE J-820, Dainippon Ink and Chemicals, Incorporated), and 5.7 g of xylene (JIS guaranteed reagent) were mixed. The powder was dispersed using a paint conditioner with 30 g of glass beads (1.5 mmφ) for 10 minutes, whereby a coating dispersion was prepared. The dispersibility evaluation was performed on the obtained coating dispersion with a grind gauge.

13. Settleability

The powder and water were put in a settling tube to a powder concentration of 5% by mass. The powder was dispersed and left to stand for 30 minutes.

Thereafter, the height of the water-sediment interface was measured. The settleability was evaluated from this height.

14. SEM Particle Size Distribution

The shape of the particles was observed with a field emission scanning electron microscope (JSM-7000F, JEOL Ltd.). SEM images of 10 fields of view were taken at a 5000-fold magnification. For each image, a straight line was randomly drawn and the particle sizes of five particles on the line were calculated. The particle sizes were obtained from all the 10 images in this manner, whereby the SEM particle size distribution was determined.

15. Whiteness

The hunter color values L, a and b of each of the phosphors (powders) obtained in Example 2 and Comparative Example 2 were measured with a colorimeter (SQ-2000, Nippon Denshoku Industries Co., Ltd.). The W value was calculated by Formula (1) above. Table 1 shows the results.

Example 1

An amount of 20 g of zinc oxide (fine zinc oxide, Sakai Chemical Industry Co., Ltd.), 0.077 g of zinc sulfide (RAK-T, Sakai Chemical Industry Co., Ltd.), and 0.0105 g of sodium hydrogen carbonate (JIS guaranteed reagent, Kanto Chemical Co., Inc.) were weighed and well dry-mixed over 30 minutes. All the obtained raw material powder mixture was put in an alumina crucible, heated to 800° C. at 200° C./hour in a 1% by volume H$_2$/N$_2$ atmosphere, held at this temperature for two hours, and then cooled at 200° C./hour.

The resulting fired product was crushed in a mortar and all the crushed product was put in an alumina crucible. The crushed product was then heated to 700° C. at 200° C./hour in an air atmosphere, held at this temperature for one hour, and then cooled at 200° C./hour. The resulting powder was subjected to washing with water and filtration. The cake obtained by filtration was washed until the electric conductivity was decreased to 0.5 mS/m or lower. The resulting cake was dried in a dryer at 130° C. overnight to give Phosphor A.

The above evaluation tests were performed on Phosphor A (powder). Table 1 and FIGS. 1 and 2 show the results.

Example 2

Dry mixing was performed as in Example 1 except that 0.0179 g of zinc sulfide was used. All the obtained raw material powder mixture was put in an alumina crucible, heated to 850° C. at 200° C./hour in a 1% by volume $H_2/N_2$ atmosphere, held at this temperature for two hours, and then cooled at 200° C./hour.

The resulting fired product was crushed in a mortar and all the crushed product was put in an alumina crucible. The crushed product was then heated to 700° C. at 200° C./hour in an air atmosphere, held at this temperature for one hour, and then cooled at 200° C./hour. The resulting powder was subjected to washing with water and filtration. The cake obtained by filtration was washed until the electric conductivity was decreased to 0.5 mS/m or lower. The resulting cake was dried in a dryer at 130° C. overnight to give Phosphor B.

The above evaluation tests were performed on Phosphor B (powder). Table 1 and FIGS. 1 and 5 show the results.

Example 3

An amount of 20 g of basic zinc carbonate (KCZ, Sakai Chemical Industry Co., Ltd.) and 0.056 g of zinc sulfide (RAK-T, Sakai Chemical Industry Co., Ltd.) were weighed and well dry-mixed over 30 minutes. All the obtained raw material powder mixture was put in an alumina crucible, heated to 750° C. at 200° C./hour in a 1% by volume $H_2/N_2$ atmosphere, held at this temperature for two hours, and then cooled at 200° C./hour.

The resulting fired product was crushed in a mortar and all the crushed product was put in an alumina crucible. The crushed product was then heated to 700° C. at 200° C./hour in an air atmosphere, held at this temperature for one hour, and then cooled at 200° C./hour. The resulting powder was subjected to washing with water and filtration. The cake obtained by filtration was washed until the electric conductivity was decreased to 0.5 mS/m or lower. The resulting cake was dried in a dryer at 130° C. overnight to give Phosphor C.

The above evaluation tests were performed on Phosphor C (powder). Table 1 and FIGS. 1 and 2 show the results.

Example 4

Dry mixing was performed as in Example 3. All the obtained raw material powder mixture was put in an alumina crucible, heated to 600° C. at 200° C./hour in a 1% by volume $H_2/N_2$ atmosphere, held at this temperature for six hours, and then cooled at 200° C./hour.

The resulting fired product was crushed in a mortar and all the crushed product was put in an alumina crucible. The crushed product was heated to 700° C. at 200° C./hour in an air atmosphere, held at this temperature for one hour, and then cooled at 200° C./hour. The resulting powder was subjected to washing with water and filtration. The cake obtained by filtration was washed until the electric conductivity was decreased to 0.5 mS/m or lower. The resulting cake was dried in a dryer at 130° C. overnight to give Phosphor D.

The above evaluation tests were performed on Phosphor D (powder). Table 1 and FIGS. 1 and 2 show the results.

Comparative Example 1

Dry mixing was performed as in Example 1. All the obtained raw material powder mixture was put in an alumina crucible, heated to 800° C. at 200° C./hour in a 1% by volume $H_2/N_2$ atmosphere, held at this temperature for two hours, and then cooled at 200° C./hour.

The resulting fired product was crushed in a mortar. The obtained powder was then subjected to washing with water and filtration. The cake obtained by filtration was washed until the electric conductivity was decreased to 0.5 mS/m or lower. The resulting cake was dried in a dryer at 130° C. overnight to give Phosphor E.

The above evaluation tests were performed on Phosphor E (powder). Table 1 and FIG. 1 show the results.

Comparative Example 2

Dry mixing was performed as in Example 1 except that 0.0179 g of zinc sulfide was used. All the obtained raw material powder mixture was put in an alumina crucible, heated to 850° C. at 200° C./hour in a 1% by volume $H_2/N_2$ atmosphere, held at this temperature for two hours, and then cooled at 200° C./hour.

The resulting fired product was crushed in a mortar. The obtained powder was subjected to washing with water and filtration. The cake obtained by filtration was washed until the electric conductivity was decreased to 0.5 mS/m or lower. The resulting cake was dried in a dryer at 130° C. overnight to give Phosphor F.

The above evaluation tests were performed on Phosphor F (powder). Table 1 and FIG. 1 show the results.

Example 5

An amount of 20 g of zinc oxide (fine zinc oxide, Sakai Chemical Industry Co., Ltd.), 0.077 g of zinc sulfide (RAK-T, Sakai Chemical Industry Co., Ltd.), 0.0105 g of sodium hydrogen carbonate (JIS guaranteed reagent, Kanto Chemical Co., Inc.), and 0.4309 g of potassium carbonate (JIS guaranteed reagent, Takasugi Pharmaceutical Co., Ltd.) were weighed and well dry-mixed over 30 minutes. All the obtained raw material powder mixture was put in an alumina crucible, heated to 850° C. at 200° C./hour in a 1% by volume $H_2/N_2$ atmosphere, held at this temperature for two hours, and then cooled at 200° C./hour. The resulting fired product was crushed in a mortar and all the crushed product was put in an alumina crucible. The resulting powder was then subjected to washing with water and filtration. The cake obtained by filtration was washed until the electric conductivity was decreased to 0.5 mS/m or lower. The resulting cake was dried in a dryer at 130° C. overnight. The dried powder was then heated to 700° C. at 200° C./hour in an air atmosphere, held at temperature for one hour, and then cooled at 200° C./hour. Thus, Phosphor G was obtained.

Figure 4:
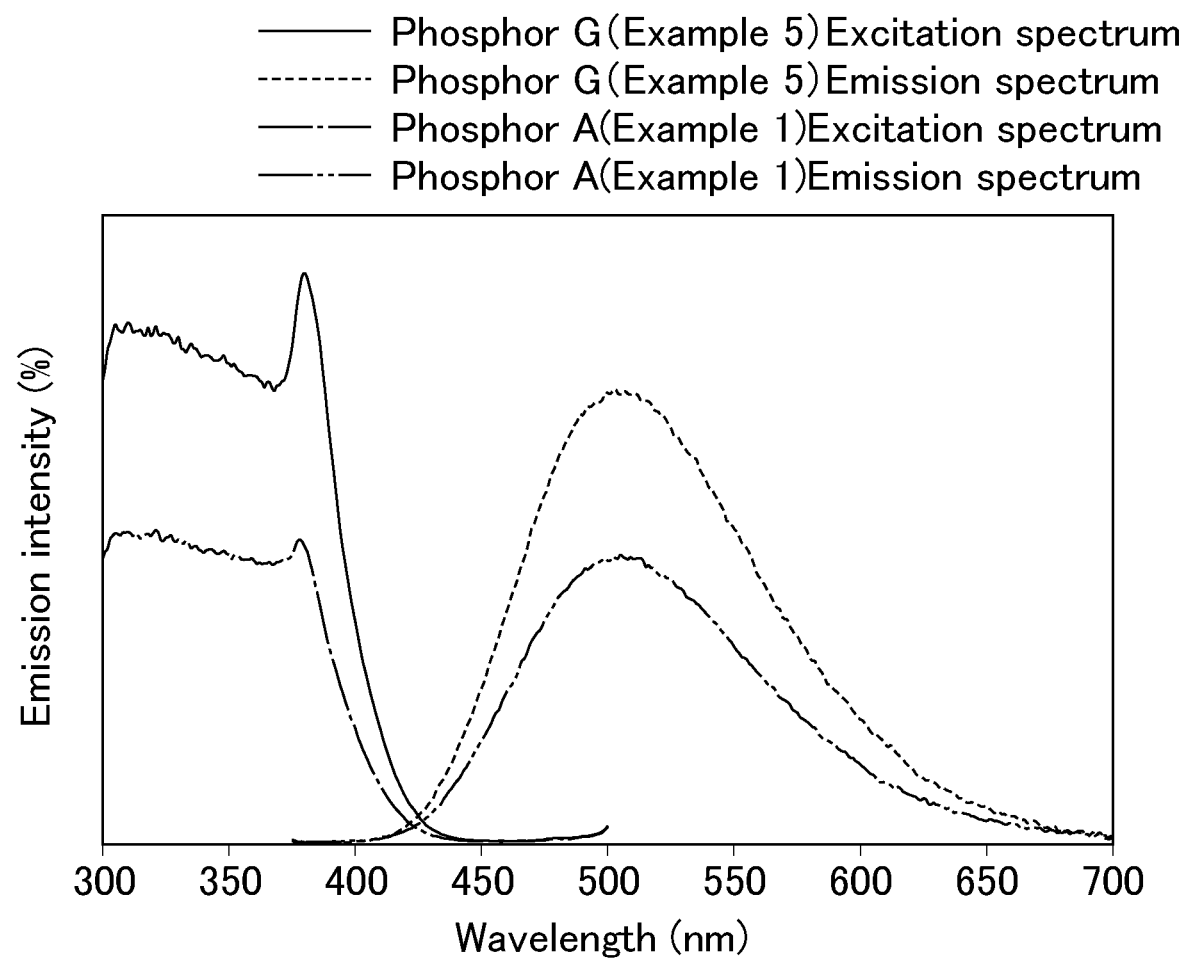
FIG. 4 shows excitation and emission spectra of Phosphor G obtained in Example 5. For comparison, FIG. 4 also shows excitation and emission spectra of Phosphor A obtained in Example 1.

The resulting potassium-added phosphor (phosphor G) (powder) was subjected to the PL evaluation test and the tests in accordance with Standards of Quasi-drug Ingredients as in Example 1. Table 1 shows the results. FIG. 3 shows a SEM photograph of Phosphor G. FIG. 4 shows excitation and emission spectra of Phosphor G in the PL evaluation (FIG. 4 also shows excitation and emission spectra of Phosphor A obtained in Example 1 for comparison). FIG. 5 shows a reflectance spectrum of Phosphor G in the evaluation of the infrared blocking performance.

Comparative Example 3

Dry mixing was performed as in Example 5. All the obtained raw material powder mixture was put in an alumina crucible, heated to 850° C. at 200° C./hour in a 1% by volume $H_2/N_2$ atmosphere, held at this temperature for two hours, and then cooled at 200° C./hour.

The resulting fired product was crushed in a mortar and all the obtained powder was put in an alumina crucible. The powder was then subjected to washing with water and filtration. The cake obtained by filtration was washed until the electric conductivity was decreased to 0.5 mS/m or lower. The resulting cake was dried in a dryer at 130° C. overnight to give Phosphor H.

Phosphor H thus obtained was subjected to the PL evaluation test and the tests in accordance with Standards of Quasi-drug Ingredients as in Example 1. Table 1 shows the results. FIG. 6 shows a SEM photograph of Phosphor H.

and $D_{50}$ of the phosphor. FIG. 7(c) is a graph showing the relation between firing temperature and the BET diameter of the phosphor. FIG. 7(d) is a graph showing the relation between the firing temperature and the sulfur content of the phosphor.

In FIGS. 7 to 10(a), the emission intensity of the phosphor is a relative emission intensity with the emission intensity of STD (standard) at the maximum emission wavelength taken as 100. In FIG. 7(a), STD was powder obtained under the same conditions as in Example 1 except that air firing was not performed. The results of STD were shown below the graphs in FIG. 7.

Example 7

Phosphors were obtained as in Example 2 except that the air firing temperature in Example 2 (700° C.) was varied within the range of 500° C. to 1000° C. FIG. 8(a) is a graph showing the relation between the firing temperature and the emission intensity of the phosphor. FIG. 8(b) is a graph showing the relation between the firing temperature and the BET specific surface area of the phosphor. FIG. 8(c) is a graph showing the relation between the firing temperature

TABLE 1

| | Name | | Example 1 Phosphor A | Example 2 Phosphor B | Example 3 Phosphor C | Example 4 Phosphor D | Comparative Example 1 Phosphor E |
|---|---|---|---|---|---|---|---|
| Powder physical properties | Internal quantum efficiency | % | 26.3 | 35.0 | 8.3 | 1.3 | 24.8 |
| | Emission intensity | % | 107 | 144 | 32 | 6 | 100 |
| | Dominant wavelength (nm) | nm | 505 | 505 | 505 | 505 | 508 |
| | BET specific surface area | m²/g | 2.50 | 0.90 | 3.77 | 7.79 | 2.52 |
| | BET diameter | μm | 0.42 | 1.18 | 0.28 | 0.14 | 0.42 |
| | $D_{50}$ | μm | 1.48 | 3.54 | 0.64 | 0.37 | 1.43 |
| | S content | ppm | 178 | 251 | — | — | 1325 |
| | Whiteness (W) | — | — | 97 | — | — | — |
| Test in accordance with Standards of Quasi-drug Ingredients | (1) Dilute sulfuric acid dissolution test | | Dissolved | Dissolved | Dissolved | Dissolved | Clouded |
| | (2) Acetic acid dissolution test | | Dissolved | Dissolved | Dissolved | Dissolved | Clouded |

| | Name | | Comparative Example 2 Phosphor F | Example 5 Phosphor G | Comparative Example 3 Phosphor H | Example 10 Phosphor I | Example 16 Phosphor J |
|---|---|---|---|---|---|---|---|
| Powder physical properties | Internal quantum efficiency | % | 31.4 | 41.0 | 40.5 | 35.1 | 33.8 |
| | Emission intensity | % | 135 | 189 | 162 | 156 | 150 |
| | Dominant wavelength (nm) | nm | 507 | 506 | 506 | 507 | 506 |
| | BET specific surface area | m²/g | 0.90 | 0.50 | 0.96 | 1.41 | 0.46 |
| | BET diameter | μm | 1.18 | 2.10 | 1.10 | 0.75 | 2.29 |
| | $D_{50}$ | μm | 3.97 | 7.30 | 7.12 | 2.47 | 6.41 |
| | S content | ppm | 308 | — | — | — | — |
| | Whiteness (W) | — | 92 | — | — | — | — |
| Test in accordance with Standards of Quasi-drug Ingredients | (1) Dilute sulfuric acid dissolution test | | Dissolved | Dissolved | Clouded | Dissolved | Dissolved |
| | (2) Acetic acid dissolution test | | Clouded | Dissolved | Clouded | Dissolved | Dissolved |

The emission intensity in Table 1 is a relative emission intensity (%), with the emission intensity of Phosphor E obtained in Comparative Example 1 at the dominant wavelength taken as 100%.

Example 6

In order to study the relation between the firing temperature in the air firing and physical properties of the resulting phosphor, phosphors were obtained as in Example 1 except that the air firing temperature in Example 1 (700° C.) was varied within the range of 500° C. to 1000° C. FIG. 7(a) is a graph showing the relation between the firing temperature and the emission intensity of the phosphor. FIG. 7(b) is a graph showing the relation between the firing temperature and the BET diameter of the phosphor. FIG. 8(d) is a graph showing the relation between the firing temperature and the sulfur content of the phosphor.

In FIG. 8(a), STD was powder obtained under the same conditions as in Example 2 except that air firing was not performed. The results of STD were shown below the graphs in FIG. 8.

Example 8

Phosphors were obtained as in Example 3 except that the air firing temperature in Example 3 (700° C.) was varied within the range of 500° C. to 900° C. FIG. 9(a) is a graph showing the relation between the firing temperature and the emission intensity of the phosphor. FIG. 9(b) is a graph showing the relation between the firing temperature and the BET specific surface area of the phosphor. FIG. 9(c) is a graph showing the relation between the firing temperature and the BET diameter of the phosphor. FIG. 9(d) is a graph showing the relation between the firing temperature and the sulfur content of the phosphor.

In FIG. 9(a), STD was powder obtained under the same conditions as in Example 3 except that air firing was not performed. The results of STD were shown below the graphs in FIG. 9.

Example 9

Phosphors were obtained as in Example 4 except that the air firing temperature in Example 4 (700° C.) was varied within the range of 500° C. to 900° C. FIG. 10(a) is a graph showing the relation between the firing temperature and the emission intensity of the phosphor. FIG. 10(b) is a graph showing the relation between the firing temperature and the BET specific surface area of the phosphor. FIG. 10(c) is a graph showing the relation between the firing temperature and the BET diameter of the phosphor.

Figure 10:
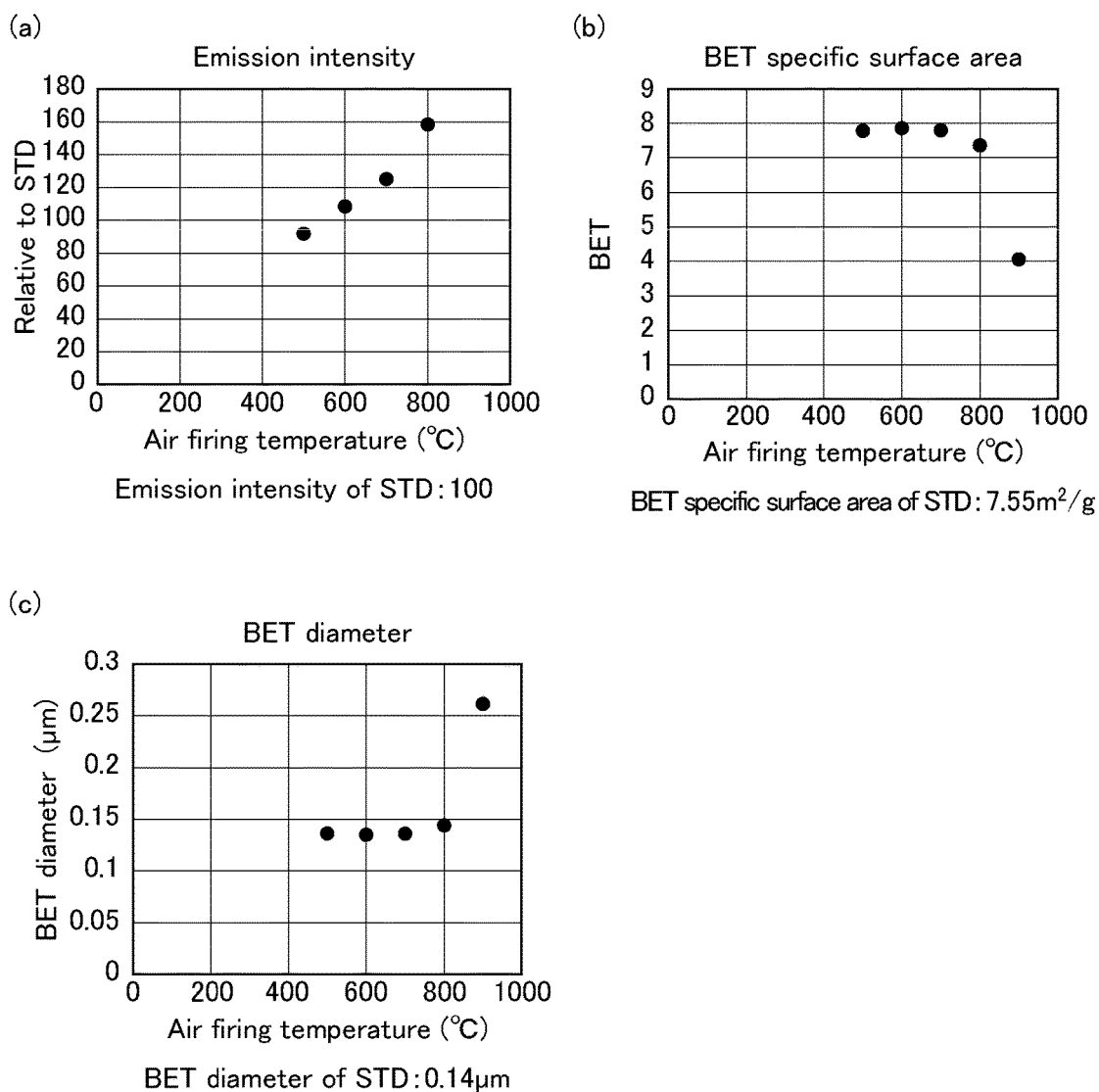
FIG. 10 shows graphs of the relation between the air firing temperature and phosphor physical properties in Example 4 (Example 9).

In FIG. 10(a), STD was powder obtained under the same conditions as in Example 4 except that air firing was not performed. The results of STD were shown below the graphs in FIG. 10.

Example 10

An amount of 20 g of zinc oxide (fine zinc oxide, Sakai Chemical Industry Co., Ltd.), 0.077 g of zinc sulfide (RAK-T, Sakai Chemical Industry Co., Ltd.), and 0.0105 g of sodium hydrogen carbonate (guaranteed reagent, Kanto Chemical Co., Inc.) were weighed and well dry-mixed over 30 minutes. All the obtained raw material powder mixture was put in an alumina crucible, heated to 850° C. at 200° C./hour in a 1% by volume $H_2/N_2$ atmosphere, held at this temperature for two hours, and then cooled at 200° C./hour. The resulting fired product was crushed in a mortar and all the crushed product was put in an alumina crucible. The crushed product was then heated to 700° C. at 200° C./hour in an air atmosphere, held at this temperature for one hour, and then cooled at 200° C./hour. The resulting powder was then subjected to washing with water and filtration. The cake obtained by filtration was washed until the electric conductivity was decreased to 0.5 mS/m or lower. The resulting cake was dried in a dryer at 130° C. overnight to give Phosphor I. Table 1 shows physical properties of Phosphor I.

Example 11

Coating film A was produced using Phosphor A obtained in Example 1. The film was produced by the same method as that used for producing the evaluation film described in "9. UV blocking performance". The PL evaluation test was performed on Coating film A. Table 2 shows the results.

Example 12

Coating film B was produced as in Example 11 except that Phosphor B obtained in Example 2 was used. The PL evaluation test was performed on Coating film B. Table 2 shows the results.

Example 13

Coating film C was produced as in Example 11 except that Phosphor C obtained in Example 3 was used. The PL evaluation test was performed on Coating film C. Table 2 shows the results.

Example 14

Coating film D was produced as in Example 11 except that Phosphor D obtained in Example 4 was used. The PL evaluation test was performed on Coating film D. Table 2 shows the results.

Example 15

Coating film I was produced as in Example 11 except that Phosphor I obtained in Example 10 was used. The PL evaluation test was performed on Coating film I. Table 2 shows the results.

TABLE 2

|  |  | Phosphor | | Coating film |
| --- | --- | --- | --- | --- |
|  | Name | BETdiameter (μm) | Emission intensity (%) | Emission intensity (%) |
| Example 11 | Phosphor A | 0.42 | 107 | 100 |
| Example 12 | Phosphor B | 1.18 | 144 | 98 |
| Example 13 | Phosphor C | 0.28 | 32 | 44 |
| Example 14 | Phosphor D | 0.14 | 6 | 11 |
| Example 15 | Phosphor I | 0.75 | 156 | 115 |

In Table 2, the emission intensity (emission intensity at the dominant wavelength) of the coating films of Examples 12 to 15 is a relative emission intensity (%) with the emission intensity of the coating film obtained in Example 11 at the dominant wavelength taken as 100%. Table 2 also shows, for reference, the BET diameter and the emission intensity at the dominant wavelength of Phosphors A to D and I shown in Table 1.

FIGS. 11(a) and 11(b) are graphs based on the results shown in Table 2. FIG. 11(a) is a graph for investigation of the relation between the particle size (BET diameter) of a phosphor (powder) and the emission intensity of a coating film produced therefrom. FIG. 11(b) is a graph for investigation of the relation between the BET diameter of a powder and the emission intensity of the powder itself.

Example 16

An amount of 2000 g of zinc oxide (fine zinc oxide, Sakai Chemical Industry Co., Ltd.), 7.8 g of zinc sulfide (RAK-T, Sakai Chemical Industry Co., Ltd.), and 84.8 g sodium hydrogen carbonate (Takasugi Pharmaceutical Co., Ltd.) were weighed and dry-mixed with a V blender over 10 minutes. An amount of 1500 g of the resulting raw material powder mixture was put in an alumina sagger, heated to 840° C. at 150° C./hour in a 3% by volume $H_2/N_2$ atmosphere, held at this temperature for two hours, and then cooled at 150° C./hour.

The resulting fired product was wet-crushed with a planetary ball mill and washed until the electric conductivity was decreased to 0.5 mS/m or lower. The resulting cake was dried in a dryer at 130° C. overnight. All the dried powder was put in an alumina sagger. The powder was then heated to 700° C. at 150° C./hour in an air atmosphere, held at this temperature for one hour, and then cooled at 150° C./hour. The resulting powder was subjected to washing with water and filtration. The resulting cake was dried in a dryer at 130° C. overnight to give Phosphor J. Table 1 shows the physical properties of Phosphor J.

Usage Example 1

A solid cosmetic product having the composition shown in Table 3 was produced. The presence or absence of emission under UV irradiation and the quality of emission upon application to the skin were evaluated.
[Production Method]
The components 1 to 14 were uniformly mixed and pressed to provide a foundation (solid cosmetic product).
[Evaluation Method]
(Presence or Absence of Emission Upon UV Irradiation)
An amount of 0.3 g of the solid cosmetic product obtained in the usage example was uniformly applied to an artificial skin and irradiated with UV light at a wavelength of 365 nm and an emission intensity of 720 µW/cm$^2$ using an UV lamp (Compact UV Lamp, 4 W, UVGL-25, 254/365 nm, 100 V, Funakoshi Co., Ltd.). The presence or absence of emission was checked.
(Quality of Emission Upon Application)
A small amount of the powder was put on the skin and spread with a finger. The skin with the applied powder was irradiated with an UV lamp and the quality of emission was checked. The evaluation criteria were as follows.
Good: Uniform, fine sparkles of light were observed.
Fair: Rather uniform, fine sparkles of light were observed.
Poor: Rough sparkles of light were observed.

TABLE 3

| | Product name | Amount |
|---|---|---|
| 1 | Flake-shaped barium sulfate (Sakai Chemical Industry Co., Ltd., H-LFM) | 20 |
| 2 | Pigment grade titanium dioxide (Sakai Chemical Industry Co., Ltd., MKR-1S) | 8.5 |
| 3 | Spherical calcium carbonate (Sakai Chemical Industry Co., Ltd., SCS-M5) | 7 |
| 4 | Hexagonal flake-shaped zinc oxide (Sakai Chemical Industry Co., Ltd., XZ-100F-LP) | 5 |
| 5 | Zinc stearate (Sakai Chemical Industry Co., Ltd., SPZ-100F) | 1.5 |
| 6 | Talc | 30 |
| 7 | Sericite | 9.3 |
| 8 | Silicone elastomer | 4 |
| 9 | Boron nitride | 3 |
| 10 | Iron oxide | 2.4 |
| 11 | Squalane | 2 |
| 12 | Silicone-acrylic copolymer | 2 |
| 13 | Methylparaben | 0.3 |
| 14 | Zinc oxide Phosphor J (BET diameter: 2.29 µm) | 5 |
| | Presence or absence of emission under UV irradiation | Present |
| | Quality of emission upon application to skin | Good |

The examples and comparative examples revealed the following facts.

In Examples 1 to 4, the phosphors were produced by the production method of the present invention. Comparative Examples 1 and 2 were mainly different from Examples 1 and 2 in that no oxygen firing was performed after reduction firing. Table 1 shows that the phosphors obtained in Comparative Examples 1 and 2 had a great sulfur content and failed to comply with the purity requirements of "Carbonate, and clarity and color of solution" and "Lead" specified in "Zinc Oxide" in Japanese Standards of Quasi-drug Ingredients (2006). In contrast, the phosphors obtained in Examples 1 and 2 had a small particle size and a sufficiently reduced sulfur content, complying with purity requirements. Moreover, the phosphors were sufficiently improved in internal quantum efficiency and emission intensity as compared with Comparative Examples 1 and 2 and also had a high whiteness. The phosphors obtained in Examples 3 and 4 had an even smaller particle size than those obtained in Examples 1 and 2, but complied with the purity requirements and thus were shown to have a high level of safety. FIG. 2 shows that the phosphors obtained in Examples 1, 3 and 4 had excellent UV blocking properties. FIG. 5 shows the phosphor obtained in Example 2 had excellent infrared blocking properties. In FIG. 2, the smaller the particle size is, the smaller the transmittance in the UV region is. This confirmed that a phosphor with a smaller particle size has higher UV blocking properties.

These facts show that the production method of the present invention easily and simply provides a zinc oxide phosphor having a high level of safety and a high emission intensity.

The same tendency was observed in the cases where potassium was added (see Example 5 and Comparative Example 3 in Table 1). That is, it was shown that the production method of the present invention, which includes reduction firing followed by oxygen firing, easily and simply provides a zinc oxide phosphor having a high level of safety and a high emission intensity. It was also shown that further performing the potassium adding step in the production method of present invention tends to improve the emission intensity and promote the growth of particles (see Table 1 and FIGS. 3 and 4), and further improves the infrared blocking properties (see FIG. 5).

FIGS. 7 to 10 show that the firing temperature in the oxygen-containing atmosphere is also an important factor for achieving even higher physical properties of a phosphor. In particular, when the firing temperature is 500° C. or higher and lower than 1000° C., the resulting zinc oxide phosphor has a reduced sulfur content and thereby an improved level of safety, while having an even higher emission intensity and an even smaller particle size.

In addition, the phosphors obtained in Examples 1 to 4, 10 and 16 were found to have excellent dispersibility and improved settleability (not shown in the table or figures). The phosphors obtained in Examples 1 to 10 and 16 were found to comply with all the requirements specified in "Zinc Oxide" in the Japanese Standards of Quasi-drug Ingredients (2006), including those other than the purity requirements of "Carbonate, and clarity and color of solution" and "Lead". The phosphors obtained in Examples 1 to 10 and 16 were found to pass the test of the "Carbonates and substances insoluble in acids" section among the tests specified in "Zinc oxide" in European Pharmacopeia.

Table 2 and FIG. 11 show that the emission intensity of the coating film containing the phosphor (powder) was also affected by the particle size of the powder, regardless of the emission intensity of the powder itself. In particular, it was found that a coating film containing a powder with a BET diameter of 0.4 to 1.2 µm has an even higher emission intensity.

Table 3 shows that the solid cosmetic product produced using the phosphors (powder) emits light under UV irradiation and emits fine sparkles of light when applied to the skin.

The invention claimed is:

1. A method for producing a zinc oxide phosphor, comprising:
   a raw material mixing step of mixing an oxygen-containing zinc compound and a sulfur-containing compound; and
   a firing step of firing the raw material mixture obtained in the raw material mixing step,
   the firing step including firing in a reducing atmosphere followed by firing in an oxygen-containing atmosphere.

2. The method for producing a zinc oxide phosphor according to claim 1,
   wherein the firing in an oxygen-containing atmosphere is performed at a firing temperature of 500° C. or higher and lower than 1000° C.

3. The method for producing a zinc oxide phosphor according to claim 1,
   wherein the zinc oxide phosphor is a cosmetic raw material.

4. A zinc oxide phosphor which complies with the purity requirements of "Carbonate, and clarity and color of solution" and "Lead" specified in "Zinc Oxide" in Japanese Standards of Quasi-drug Ingredients (2006),
   wherein the zinc oxide phosphor has an internal quantum efficiency of 10% or higher.

5. The zinc oxide phosphor according to claim 4, which has a BET diameter of 1.2 μm or smaller.

6. A solid cosmetic product comprising the zinc oxide phosphor according to claim 4.

7. A method for producing a solid cosmetic product, comprising the step of mixing raw materials including a zinc oxide phosphor obtained by the method according claim 1, talc, sericite, and an oil component and compression-molding the raw material mixture.

8. A zinc oxide phosphor which satisfies the following:
   when 2.0 g of the zinc oxide phosphor is shaken with 10 mL of pure water, followed by addition of 30 mL of 10% sulfuric acid and heating on a water bath with stirring, no effervescence occurs or the solution is clear and colorless; and
   when 20 mL of pure water is added to 2.0 g of the zinc oxide phosphor, followed by addition, with stirring, of 5 mL of glacial acetic acid and heating on a water bath to effect dissolution, addition of five drops of a potassium chromate reagent to the solution after cooling produces no turbidity or cloudiness,
   wherein the zinc oxide phosphor has an internal quantum efficiency of 10% or higher.

* * * * *